(12) United States Patent
Wang et al.

(10) Patent No.: US 10,690,647 B2
(45) Date of Patent: Jun. 23, 2020

(54) CHEMICAL SENSOR FOR HEAVY METAL DETECTION

(71) Applicants: Nanyang Technological University, Singapore (SG); Massachusetts Institute of Technology, Cambridge, MA (US)

(72) Inventors: Nan Wang, Singapore (SG); Jianmin Miao, Singapore (SG); Michael S. Triantafyllou, Cambridge, MA (US)

(73) Assignees: NANYANG TECHNOLOGICAL UNIVERSITY, Singapore (SG); MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 12 days.

(21) Appl. No.: 15/741,977

(22) PCT Filed: Jul. 5, 2016

(86) PCT No.: PCT/SG2016/050312
§ 371 (c)(1),
(2) Date: Jan. 4, 2018

(87) PCT Pub. No.: WO2017/007427
PCT Pub. Date: Jan. 12, 2017

(65) Prior Publication Data
US 2018/0196025 A1 Jul. 12, 2018

Related U.S. Application Data

(60) Provisional application No. 62/188,824, filed on Jul. 6, 2015.

(51) Int. Cl.
*G01N 33/18* (2006.01)
*G01N 27/42* (2006.01)

(52) U.S. Cl.
CPC ......... *G01N 33/1813* (2013.01); *G01N 27/42* (2013.01); *G01N 33/1893* (2013.01)

(58) Field of Classification Search
CPC ........ G01N 33/54393; G01N 27/44791; B01L 2300/0861; B01L 2300/087; B01L 2300/0877; B01L 2200/027; B01L 9/527
See application file for complete search history.

(56) References Cited

U.S. PATENT DOCUMENTS 6,299,757 B1 * 10/2001 Feldman ................ C12Q 1/001
205/775
9,234,861 B2 * 1/2016 Kanemoto ............. G01N 27/30
(Continued)

FOREIGN PATENT DOCUMENTS

WO 2015/072186 A1 5/2015

OTHER PUBLICATIONS

International Search Report in International Application No. PCT/SG2016/050312, dated Aug. 20, 2016.
(Continued)

*Primary Examiner* — Luan V Van
*Assistant Examiner* — Caitlyn Mingyun Sun
(74) *Attorney, Agent, or Firm* — Venable LLP; Henry J. Daley

(57) ABSTRACT

A chemical sensor for heavy metal detection is provided. The chemical sensor includes an inlet, a chamber in fluid communication with the inlet, and an outlet in fluid communication with the chamber. A working electrode is provided in the chamber. The working electrode includes a plurality of protrusions extending into a fluid flow path in the chamber beyond a boundary layer of the fluid flow path. The chemical sensor also includes a reference electrode, a counter electrode, and a plurality of contact pads electrically
(Continued)

connected to respective ones of the working electrode, the reference electrode and the counter electrode.

11 Claims, 17 Drawing Sheets

(56) References Cited

U.S. PATENT DOCUMENTS

| | | | |
|---|---|---|---|
| 9,874,541 B2* | 1/2018 | Raguse | G01N 27/4146 |
| 2003/0003026 A1* | 1/2003 | Parce | G01N 27/44791 |
| | | | 422/400 |
| 2011/0042237 A1* | 2/2011 | Fukuda | B01L 3/5027 |
| | | | 205/775 |
| 2013/0199264 A1 | 8/2013 | Seike | |
| 2015/0137189 A1 | 5/2015 | Pace et al. | |

OTHER PUBLICATIONS

Cox, "Hydrodynamic aspects of fish olfaction," J. R. Soc. Interface, 5: 575-593 (2008).

Hamdani et al., "The functional organization of the olfactory system," Progress in Neurobiology, 82: pp. 80-86 (2007).

Jang et al., "State-of-the-art lab chip sensors for environmental water monitoring," Meas. Sci. Technol. 22: pp. 1-18 (2011).

Kokkinos et al., "Lithographically fabricated disposable bismuth-film electrodes for the trace determination of Pb(II) and Cd(II) by anodic stripping voltammetry," Electrochimeca Acta, 53: pp. 5294-5299 (2008).

Schluessel et al., "Morphometric and Ultrastructural Comparison of the Olfactory System in Elasmobranchs: The Significance of Structure-Function Relationships Based on Phylogeny and Ecology," Journal of Morphology, 269: pp. 1365-1386 (2008).

Timm et al., "A comparative morphological study of head shape and olfactory cavities of sharks inhabiting benthic and coastal/pelagic environments," Journal of Experimental Marine Biology and Ecology, 414-415: pp. 75-84 (2012).

Wan et al., "Design of a novel hybrid sensor with microelectrode array and LAPS for heavy metal determination using multivariate nonlinear calibration," Sensors and Actuators B 192: pp. 755-761 (2014).

Wang et al., "Miniaturized chemical sensor with bio-inspired micropillar working electrode array for lead detection," Sensors and Actuators B: Chemical, vol. 233, pp. 249-256 (Apr. 2016).

Wang et al., "Shark-inspired mems chemical sensor with epithelium-like micropillar electrode array for lead detection," 2015 Transducers—2015 18th International Conference on Solid-State Sensors, Actuators and Microsystems (Transducers), pp. 1464-1467 (Jun. 2015).

Zeiske et al., "Functional mophology of the olfactory organ of two carcharhinid shark species," Can. J. Zool. vol. 65, pp. 2406-2412 (1987).

"Environmental sensors for air and water pollution monitoring," Retrieved on Aug. 24, 2016 from <https://seminar.censam.sg/workshop2015/download/CENSAM%20Workshop%202015%20-%20Jianmin%20Mao.pptx>, slides 8 and 9.

* cited by examiner

CHEMICAL SENSOR FOR HEAVY METAL DETECTION

This application is a U.S. National Stage Application under 35 U.S.C. § 371 of PCT/SG2016/050312, filed on Jul. 5, 2016, the entire content of which is hereby incorporated by reference, and claims the benefit of U.S. Provisional Application No. 62/188,824 filed Jul. 6, 2015.

FIELD OF THE INVENTION

The present invention relates to chemical sensors in general and more particularly to chemical sensors for heavy metal detection.

BACKGROUND OF THE INVENTION

Due to the non-biodegradable nature of heavy metals and the serious health effects of heavy metal contamination, continuous monitoring of pollution levels at different locations of crucial water areas is of foremost importance. Conventional water quality monitoring is typically carried out by first collecting water samples from several fixed or random sites according to the types of pollution problems that may be encountered, after which packaged samples are transported to localized laboratories. Thereafter, comprehensive experiments are performed by specialists for the purpose of providing detailed information on overall water quality of a particular region.

One drawback of conventional water contamination surveillance is potential distortion of test results as unpredictable physical, chemical and/or biological reactions may occur in the samples during the significant lapse of time from sample collection to testing.

Furthermore, water specimen collection is time consuming and labour intensive because both time and labour are required to gather sufficient samples at various depths and from numerous waterways.

Another drawback of conventional water pollution monitoring is the limited number of water testing facilities due to the significant equipment and labour cost of providing and operating a water testing facility.

It is therefore desirable to provide a miniaturized, sensitive and disposable chemical sensor for on-site or in-situ heavy metal detection.

SUMMARY OF THE INVENTION

Accordingly, in a first aspect, the present invention provides a chemical sensor including an inlet, a chamber in fluid communication with the inlet, and an outlet in fluid communication with the chamber. A working electrode is provided in the chamber. The working electrode includes a plurality of protrusions extending into a fluid flow path in the chamber beyond a boundary layer of the fluid flow path. The chemical sensor also includes a reference electrode, a counter electrode, and a plurality of contact pads electrically connected to respective ones of the working electrode, the reference electrode and the counter electrode.

Other aspects and advantages of the invention will become apparent from the following detailed description, taken in conjunction with the accompanying drawings, illustrating by way of example the principles of the invention.

BRIEF DESCRIPTION OF THE DRAWINGS

Embodiments of the invention will now be described, by way of example only, with reference to the accompanying drawings, in which.

DETAILED DESCRIPTION OF EXEMPLARY EMBODIMENTS

The detailed description set forth below in connection with the appended drawings is intended as a description of presently preferred embodiments of the invention, and is not intended to represent the only forms in which the present invention may be practiced. It is to be understood that the same or equivalent functions may be accomplished by different embodiments that are intended to be encompassed within the scope of the invention.

Figure 1A:
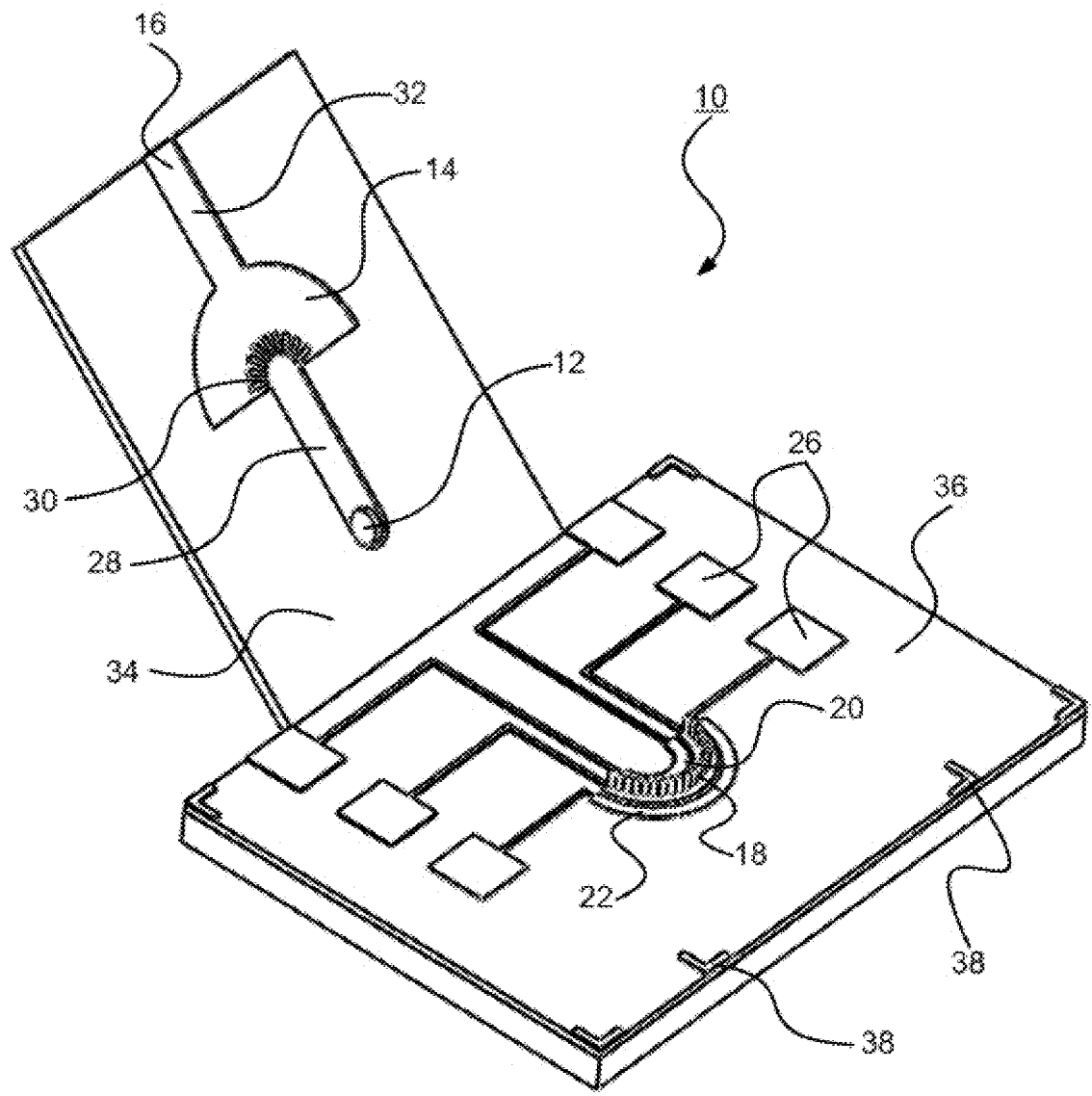
FIGS. 1A through 1C are schematic diagrams illustrating a chemical sensor in accordance with one embodiment of the present invention.

Referring now to FIG. 1A, a chemical sensor 10 for heavy metal detection is shown. The chemical sensor 10 includes an inlet 12, a chamber 14 in fluid communication with the inlet 12, and an outlet 16 in fluid communication with the chamber 14. A working electrode 18 is provided in the chamber 14. The chemical sensor 10 also includes a reference electrode 20 and a counter electrode 22.

Figure 1B:
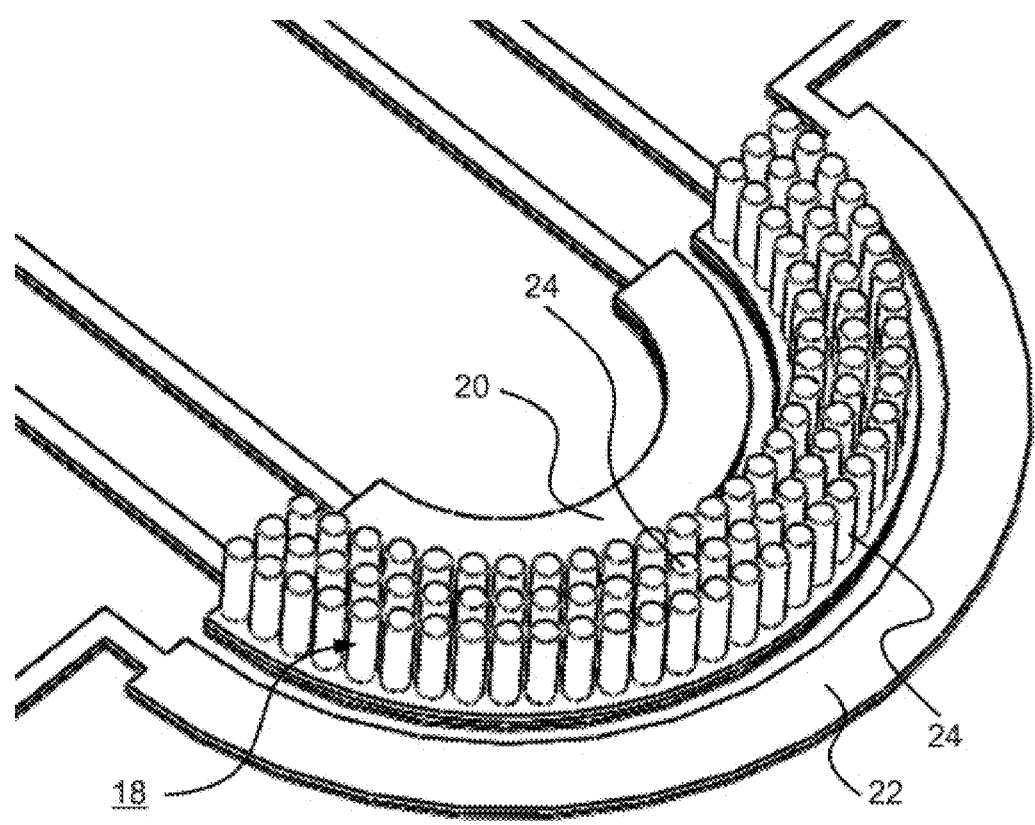

Referring now to FIG. 1B, the working electrode 18 includes a plurality of protrusions 24 extending into a fluid flow path in the chamber 14 beyond a boundary layer of the fluid flow path. In the present embodiment, each of the protrusions 24 is a column of micro dimensions. The term "micro dimensions" as used herein refers to dimensions between 1 micrometre (μm) and 1 centimetre (cm) in size. In one embodiment, each column may have a height of between about 10 microns (μm) and about 1000 μm. As can be seen from FIG. 1B, the working electrode 18 of the present embodiment is designed to have a large number of free-standing micro-sized pillar electrodes or protrusions 24 with side walls that are coated by gold, bismuth or other environmentally friendly material. The spacing between adjacent micropillars or protrusions 24 provides sufficient space for heavy metal ions dissolved in a test solution to be collected by each individual micropillar electrode or protrusion 24.

In the embodiment shown, the protrusions 24 are provided in a parabolic arrangement. The micropillar electrodes 24 are positioned in an arch or parabolic shape to take advantage of hydrodynamic principle as the velocity profile of laminar flow, which is always the case in microchannels, follows a parabolic path. In alternative embodiments, the protrusions 24 may be provided in a rectilinear arrangement, a diagonal arrangement and/or a curvilinear arrangement.

The three-dimensional arrangement of the micropillar array of working electrodes 18 successfully circumvents the problem of boundary layer effect in laminar flow, thereby maximizing the sensing capacity of the chemical sensor 10. By incorporating this high density standing structure of working electrodes 18 into the chemical sensor 10, the effective sensing area in contact with the sample solution is substantially increased, thereby significantly enhancing the sensitivity of the chemical sensor 10.

In the present embodiment, a separation between the working electrode 18 and the reference electrode 20 is about 0.1 millimetre (mm) and a separation between the working electrode 18 and the counter electrode 22 is about 0.1 mm. The separation between the working electrode 18 and the reference electrode 20 is related to the ohmic losses of the chemical sensor 10. Since the ohmic losses cannot be compensated by the measuring instrument, the separation between the working electrode 18 and the reference electrode 20 should be as minimal as possible, especially in a situation where the testing solution has very low conductivity. The reference electrode 20 should not however be positioned too close to the working electrode 18 as this would disturb the equipotential lines of the working electrode 18. Accordingly, the separation between the working electrode 18 and the reference electrode 20 may be determined based on the size and shape of the working electrode 18 and the conductivity of the testing solution. The separation between the working electrode 18 and the counter electrode 22 is not as critical as the function of the counter electrode 22 is simply to close the current circuit together with the working electrode 18. The surface area of counter electrode 22 should be large enough to ensure that the current passes through the counter electrode 22, and not the reference electrode 20. A surface area of the counter electrode 22 is preferably at least 1.5 times a surface area of the reference electrode 20 to ensure that current passes through the counter electrode 22, and not the reference electrode 20. In the present embodiment, the reference electrode 20 has a surface area of about 0.707 square millimetres ($mm^2$) and the counter electrode 22 has a surface area of about 1.649 $mm^2$. Accordingly, a surface area of the counter electrode 22 is about 2.33 times a surface area of the reference electrode 20 in the present embodiment.

Referring again to FIG. 1A, a plurality of contact pads 26 is electrically connected to respective ones of the working electrode 18, the reference electrode 20 and the counter electrode 22.

A first microfluidic channel 28 couples the inlet 12 to the chamber 14 in the present embodiment.

Figure 1C:
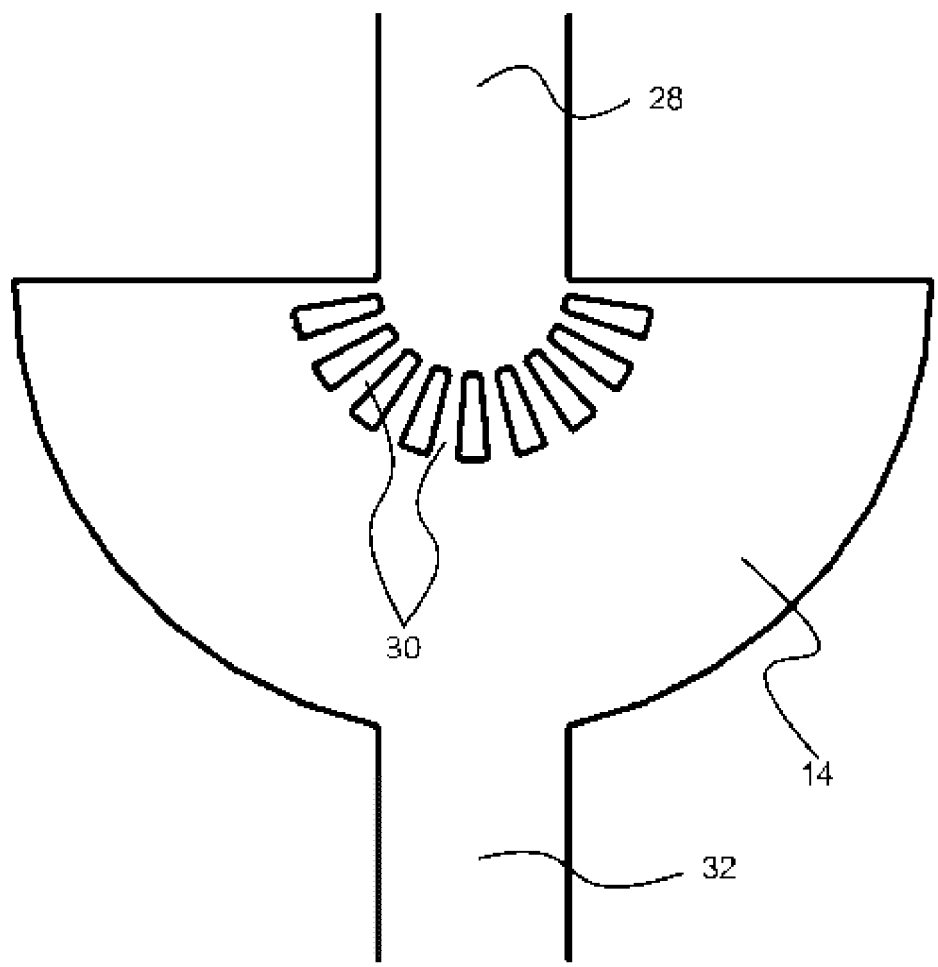

Referring now to FIG. 1C, a plurality of subchannels 30 interface the first microfluidic channel 28 and the working electrode (not shown) in the chamber 14 in the embodiment shown. Advantageously, when a sample solution is pumped into an inlet passage of the first microfluidic channel 28, the sample solution is directed to the subchannels 30 so that all the micropillar working electrodes 24 that are located at succeeding sections relative to the subchannels 30 are able to participate in the process of heavy metal ion collection. By guiding the sample solution to flow towards the micropillar electrode array 24, the effective sensing area that comes in contact with the metal ions and thus the capture sensitivity are significantly increased. Without the subchannels 30, most of the test solution only passes through the middle section of the working electrode array 24 because fluid flow within the first microfluidic channel 28 is laminar and the velocity profile of laminar flow is parabolic so fluid tends to move much faster in the middle section of the first microfluidic channel 28. Capture efficiency is thus significantly enhanced by the provision of the subchannels 30. Although ten (10) subchannels 30 are illustrated in FIG. 1C, it should be understood by those of ordinary skill in the art that the present invention is not limited by the number of subchannels 30 provided. Fewer or more subchannels 30 may be provided in alternative embodiments depending on the requirements of the chemical sensor 10.

Referring again to FIG. 1A, a second microfluidic channel 32 couples the chamber 14 to the outlet 16 in the present embodiment.

As can be seen from FIG. 1A, the chemical sensor 10 of the present embodiment includes a first portion 34 and a second portion 36. The inlet 12 and the outlet 16 are provided in the first portion 34, and the working electrode 18, the reference electrode 20 and the counter electrode 22 are provided in the second portion 36. The chamber 14 is defined between the first portion 34 and the second portion 36. In the present embodiment, a plurality of assembly marks 38 is provided as alignment reference when bringing the first portion 34 and the second portion 36 of the chemical sensor 10 together.

The chemical sensor 10 of the present embodiment is a microelectromechanical system (MEMS) with a micropillar electrode array. Advantageously, this enables quick identification of minute variations in heavy metal concentration in water samples during on-site or in-situ heavy metal detection. The sensing principle of the MEMS chemical sensor 10 is based on anodic stripping voltammetry.

In the embodiment shown, the first portion or top part 34 includes the first microfluidic channel 28 that serves as a holder for a water sample and the chamber 14 for electrochemical reaction, whilst the second portion or bottom part 36 provides a sensor base to place three types of miniaturized electrodes 18, 20 and 22 along with the contact pads 26 for applying a potential input via the reference electrode 20 and the working electrode 18 and collecting a current output through the working electrode 18 and the counter electrode 22. The function of the sensor base is to support the three primary sensing components: the working electrode 18, the reference electrode 20 and the counter electrode 22. The reference electrode 20 is to supply a reference potential value with respect to a cell potential, the working electrode 18 is to provide a suitable site for pre-deposition of specific heavy metal ions, and the counter electrode 22 is to work as a current sink during the electrochemical reaction.

Having described the various elements of the chemical sensor 10, operation of the chemical sensor 10 will now be described below.

In use, a sample solution containing a variety of heavy metal ions is pumped into the reaction chamber 14 through the inlet 12 via the first microfluidic channel 28. Specific metal ions are electroplated on the working electrode 18 during a deposition step that is controlled by the applied potential as well as deposition time. During the deposition step, the inlet 12 of the first microfluidic channel 28 is constrained so that fresh solution does not flow into the chamber 14. This is not only to minimize the volume of required sample, but also to provide sufficient time for heavy metal ions to be coated onto the surface of the working electrode 18. Thereafter, oxidation of the previously deposited metal is triggered by applying a potential with opposite polarity in comparison to the deposition potential. During this stripping step, multiple peaks of current output at different potentials at which certain species begin to be oxidized are recorded. The current signals are then converted into concentrations of specific heavy metal ions.

Fabrication of the chemical sensor 10 may be performed with the aid of MEMS technology and an example of this will now be described below.

Figure 2:
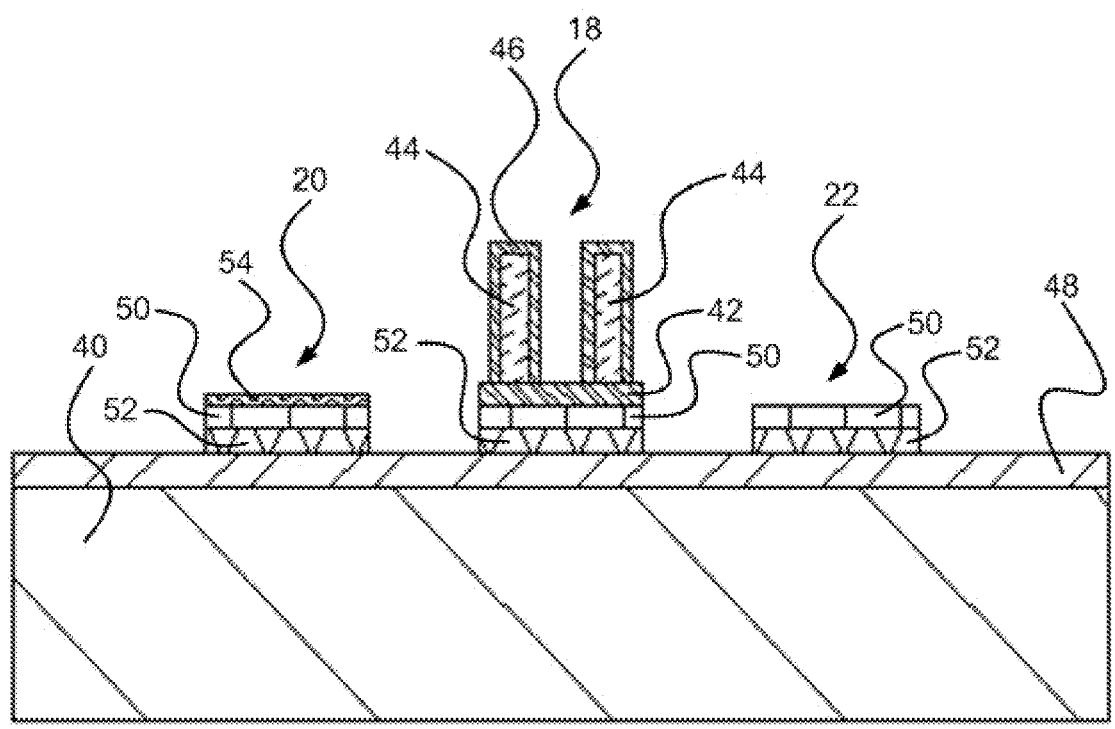
FIG. 2 is an enlarged schematic cross-sectional diagram of a working electrode, a reference electrode and a counter electrode of the chemical sensor of FIG. 1A.

Referring now to FIG. 2, the chemical sensor 10 may include a substrate 40 serving as a support. The reference electrode 20 and the counter electrode 22 may be provided on the substrate 40. The working electrode 18 of the present embodiment may be provided on the substrate 40 and may include a first electrically conductive layer 20 42, a plurality of microcolumns 44 provided on the first electrically conductive layer 42 and an electrically conductive material 46 deposited on the microcolumns 44.

More particularly, the sensor base in one embodiment of the chemical sensor 10 may be constituted of multiple layers as shown in FIG. 2 including a substrate 40 of silicon (500 μm) serving as a supporting base for an upper structure and an insulation layer 48 of silicon dioxide (1 μm) providing insulation between the working electrode 18, the reference electrode 20 and the counter electrode 22. A second electrically conductive layer 50 in the form of a gold layer (300 nanometres (nm)) supplies electrical connection to each of the working electrode 18, the reference electrode 20 and the counter electrode 22. An adhesive layer 52 of chromium (100 nm) may be provided between the insulation layer 48 and the second electrically conductive layer 50 to strengthen the adhesive force between the two. A silver with silver chloride layer 54 (500 nm) may be provided on the corresponding second electrically conductive layer 50 to form the reference electrode 20. The working electrode 18 may be formed by depositing a first electrically conductive layer 42 of bismuth or gold (400 nm) on the corresponding second electrically conductive layer 50. The microcolumns 44 may be formed on the first electrically conductive layer 42 by patterning a layer of SU-8 photoresist (100 μm) to form a micropillar array. Top and side surfaces of all the microcolumns 44 may be coated with an electrically conductive material 46 of bismuth or gold thin film (200 nm). The structure having only the second electrically conductive layer 50 serves as the counter electrode 22.

In one embodiment, the sensor base of FIG. 2 may be formed by depositing 1 μm of a silicon dioxide insulation layer by plasma-enhanced chemical vapor deposition (PECVD) on a 4 inch diameter p-type <100> silicon wafer that is thoroughly cleaned by acetone and isopropanol and rinsed with deionized (DI) water. The wafer is then moved into a hexamethyldisilazane (HDMS) chamber to promote adhesion of photoresist to the silicon wafer. Next, 5 μm of AZ 9260 positive photoresist is spin-coated on top of the insulation layer at a rotational speed of 5000 revolutions per minute (rpm) for a period of 30 seconds, followed by baking on a hotplate at 110° C. for 4 minutes. The spin-coated photoresist is then exposed to 365 nm i-line UV light and developed by a sufficient amount of 400 K photoresist developer. Strong agitation is provided to ensure that the geometric pattern printed on the plastic photomask is precisely transferred onto the photoresist. A metal layer comprising 100 nm chromium and 300 nm gold is then sputtered onto the top surface of the entire wafer by physical vapor deposition (PVD). Thereafter, the wafer is completely dipped into an acetone solution to remove all remaining photoresist and then rinsed with DI water. Up until this point, fabrication of the base electrode layer (which is also the counter electrode layer) is completed and another 5 μm of AZ 9260 positive photoresist is subsequently spin-coated on top of the base electrode layer. Once the positive photoresist on the working electrode 18 is developed by photolithography, 400 nm of bismuth or gold is sputtered onto the second-layer pattern. Removal of the previously spin-coated photoresist with the help of acetone exposes the working electrode layer. Similar processes are carried out to define the reference electrode 20.

To fabricate the micropillar array, a SU-8 2100 negative photoresist is selected to shape the core of each micropillar as SU-8 is able to produce a fine structure with stable chemical and thermal properties. Firstly, a thick layer of 100 μm of SU-8 negative photoresist is spin-coated at a rotational speed of 3000 rpm with 300 rpm/second acceleration for 30 seconds. Thereafter, the wafer is placed on a hotplate to perform soft baking. To maintain uniformity of the thickness, the baking temperature as well as the baking time is optimized by ramping up the temperature from 50 degrees Celsius (° C.) to 65° C. for 5 minutes and further to 80° C. for another 5 minutes, before holding the temperature at 90° C. for 30 minutes. When the pre-baked SU-8 layer completely cools down, photolithography with UV light is performed after which post baking is started from 50° C. The post baking conditions are similar to the soft baking conditions except that the temperature of 90° C. is held for 15 minutes. Once post baking is completed, an SU-8 developer is used to remove the unexposed portions and then fresh developer solution and isopropanol are sprayed to fully remove residual SU-8 photoresist. Following this, a new 5 μm layer of AZ 9260 positive photoresist is spin-coated to make a pattern whereby both the reference electrode 20 and the counter electrode 22 are enclosed by a positive photoresist, leaving only the working electrode 18 uncovered. Thereafter, 200 nm of bismuth or a gold thin film is sputtered to generate side walls of the micropillar array of working electrodes 18. Lastly, all the remaining positive photoresist is removed and the fabrication of the sensor base of the MEMS chemical sensor 10 is completed.

In one embodiment, a surface of the protrusions 24 may be modified by at least one of a plurality of metallic nanoparticles (for example, bismuth (Bi) nanoparticles), a two-dimensional material (for example, graphene with functional groups) and a plurality of deoxyribonucleic acid/ribonucleic acid (DNA/RNA) molecules (for example, functionalized aptamers). Advantageously, modification of surface properties of the protrusions 24 may enhance the sensitivity and/or selectivity of the chemical sensor 10 by either increasing the total surface area of the working electrode 18 or enhancing the molecular interaction between target ions and electrode surface, thereby enhancing the potential range of molecules that can be detected.

Figure 3A:
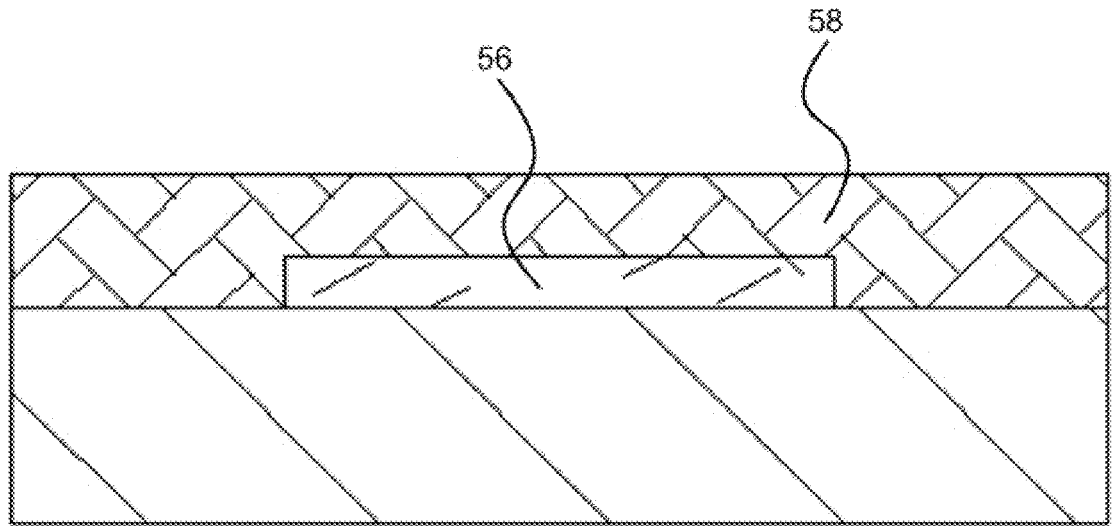
FIGS. 3A and 3B are enlarged schematic cross-sectional diagrams illustrating formation of a microfluidic channel of the chemical sensor of FIG. 1A.
Figure 3B:
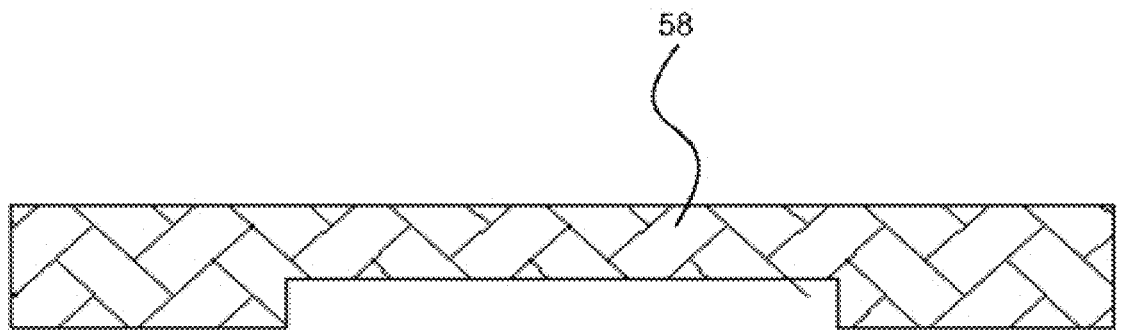

Referring now to FIGS. 3A and 3B, formation of a microfluidic channel of the chemical sensor 10 of FIG. 1A will now be described. Fabrication of the microfluidic channel is initiated by spin-coating 100 μm of a SU-8 negative photoresist 56 at a rotational speed of 3000 rpm for 30 seconds, followed by soft baking on a hotplate under the same baking protocol as employed for the fabrication of the SU-8 micropillar array. Before the photolithographic operation, the baked wafer is stored in a closed chamber at room temperature for 12 hours to diminish thermal stress induced during the pre-baking process. An SU-8 developer is then applied to selectively wash off the photoresist 56 in specific areas to form the channel shape. A polydimethylsiloxane (PDMS) solution A and solution B are uniformly mixed in a ratio of 10:1 to turn the original liquid into a material with appropriate viscosity. The blended solution is put inside a vacuum chamber as the degree of degasification has a great impact on the generation of air bubbles. Subsequently, the degassed solution 58 is slowly poured into a SU-8 mold that is confined in a petri dish with ventilation apertures. The petri dish is then shifted to an automatically-controlled oven to proceed with constant heating at 75° C. for 3 hours. Once the baked PDMS 58 is peeled off from the SU-8 mold, fabrication of the microfluidic channel that is to be assembled with the MEMS chemical sensor base of FIG. 2 is completed.

Figure 4:
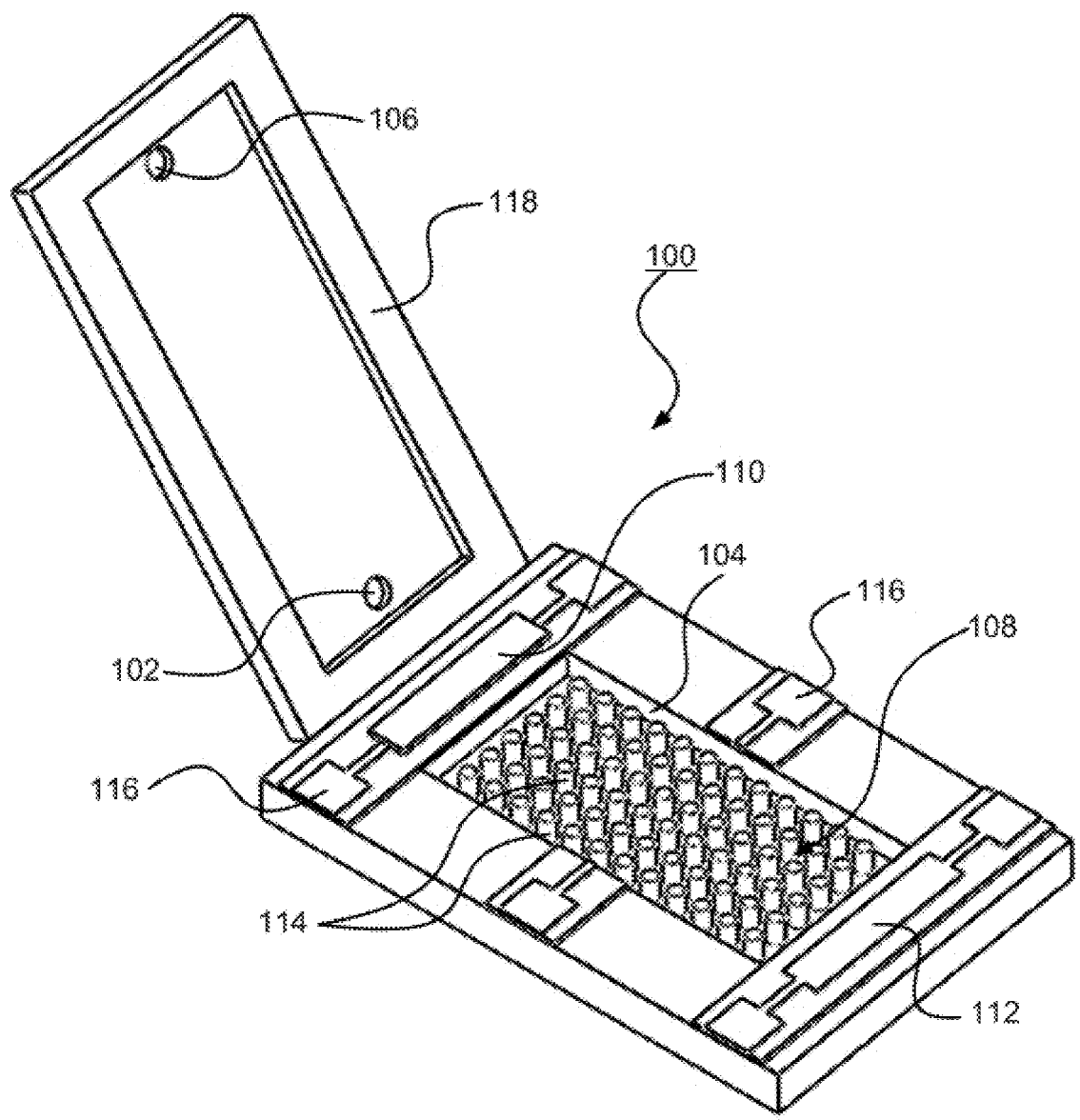
FIG. 4 is a schematic diagram of a chemical sensor in accordance with another embodiment of the present invention.

Referring now to FIG. 4, a chemical sensor 100 for heavy metal detection in accordance with another embodiment of the present invention is shown. The chemical sensor 100 includes an inlet 102, a chamber 104 in fluid communication with the inlet 102, and an outlet 106 in fluid communication with the chamber 104. A working electrode 108 is provided in the chamber 104. The chemical sensor 100 also includes a reference electrode 110 and a counter electrode 112. The working electrode 108 includes a plurality of protrusions 114 extending into a fluid flow path in the chamber 104 beyond a boundary layer of the fluid flow path. A plurality of contact pads 116 is electrically connected to respective ones of the working electrode 108, the reference electrode 110 and the counter electrode 112. The working electrode 108, the reference electrode 110 and the counter electrode 112 form a chemical sensor 100 with a three-electrode configuration. In the embodiment shown, a glass cover 118 providing the inlet 102 and the outlet 106 is attached to seal the reaction chamber 104. In the present embodiment, the protrusions 114 are arranged in an array.

In the embodiment shown, a separation between the working electrode 108 and the reference electrode 110 is about 0.4 mm and a separation between the working electrode 108 and the counter electrode 112 is about 0.4 mm.

Figure 5:
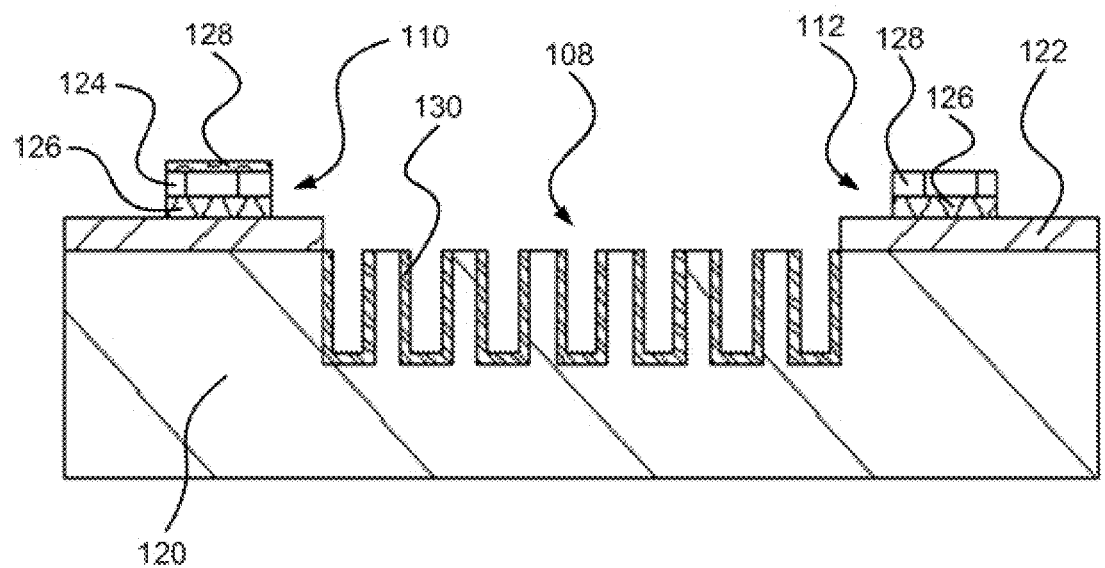
FIG. 5 is an enlarged schematic cross-sectional diagram of a working electrode, a reference electrode and a counter electrode of the chemical sensor of FIG. 4.

Referring now to FIG. 5, an enlarged schematic cross-sectional diagram illustrating the working electrode 108, the reference electrode 110 and the counter electrode 112 of the chemical sensor 100 of FIG. 4 is shown. As can be seen from FIG. 5, the chemical sensor 100 includes a substrate 120 serving as a support. The reference electrode 110 and the counter electrode 112 are provided on the substrate 120 and the working electrode 108 is provided in the substrate 120.

The chemical sensor 100 of FIGS. 4 and 5 differs from that shown in FIG. 1 in that the chemical sensor 100 merges the working electrode 108 with the sensor base to provide an embedded micropillar electrode array inside the substrate 120. In this embodiment, the substrate 120 of silicon (500 μm) not only supports an upper structure, but also provides the reaction chamber 104 for collecting heavy metal ions during electrochemical measurement. An insulation layer 122 of silicon dioxide (1 μm) is provided to insulate the working electrode 108, the reference electrode 110 and the counter electrode 112. An electrically conducive layer 124 of gold (300 nm) is provided to electrically connect the contact pads (not shown) to respective ones of the reference electrode 110 and the counter electrode 112 and an adhesive layer 126 of chromium (100 nm) may be added to reinforce adhesion of the electrically conducive layer 124 to the insulation layer 122. A silver with silver chloride layer 128 (500 nm) may be provided on the reference electrode 110, while the unmodified gold layer 124 at a second end of the substrate 120 functions as the counter electrode 112. An electrically conductive material 130 of bismuth or gold thin film (200 nm) may be electroplated on the silicon micropillar array to provide the working electrode 108.

In one embodiment, the chemical sensor 100 may be fabricated by applying PECVD to grow a silicon dioxide insulation layer 122 on top of the silicon substrate 120. A 5 μm layer of AZ 9260 positive photoresist is then spin-coated and exposed under UV light after baking on a hotplate at 110° C. for 4 minutes. To form the base electrode layer, 100 nm of chromium together with 300 nm of gold is sputtered by PVD to cover the entire wafer, after which acetone solution is sprayed to flush away all residual photoresist. Similar processing steps are performed to produce the reference electrode 110, which is made of 200 nm of silver together with 300 nm of silver chloride. Subsequently, another 5 μm of AZ 9260 positive photoresist is coated to conceal both the reference electrode 110 and the counter electrode 112 beneath the photoresist. The photoresist layer is then developed by photolithography to define the etching window of the insulation layer 122. The silicon dioxide insulation layer 122 is then etched away using the deep reactive-ion etching (DRIE) approach. Once the remaining photoresist is removed by acetone solution, a new layer of AZ 9260 positive photoresist is spin-coated for the manufacture of the silicon micropillars. Photolithography with a patterned photomask is performed to carefully open pre-specified areas for later etching. An embedded silicon micropillar array is formed by etching away portions of the silicon substrate 120. A bismuth or gold thin film is then electroplated to fill up the opening trenches so that both the bottom surface of reaction chamber 104 and the sidewalls of each silicon micropillar may function as the working electrode 108. Removal of the photoresist exposes the sensor base of the MEMS chemical sensor 100. The glass cover 118 may be assembled with the fabricated sensor base by utilizing an anodic bonding method.

EXAMPLE

Figure 6A:
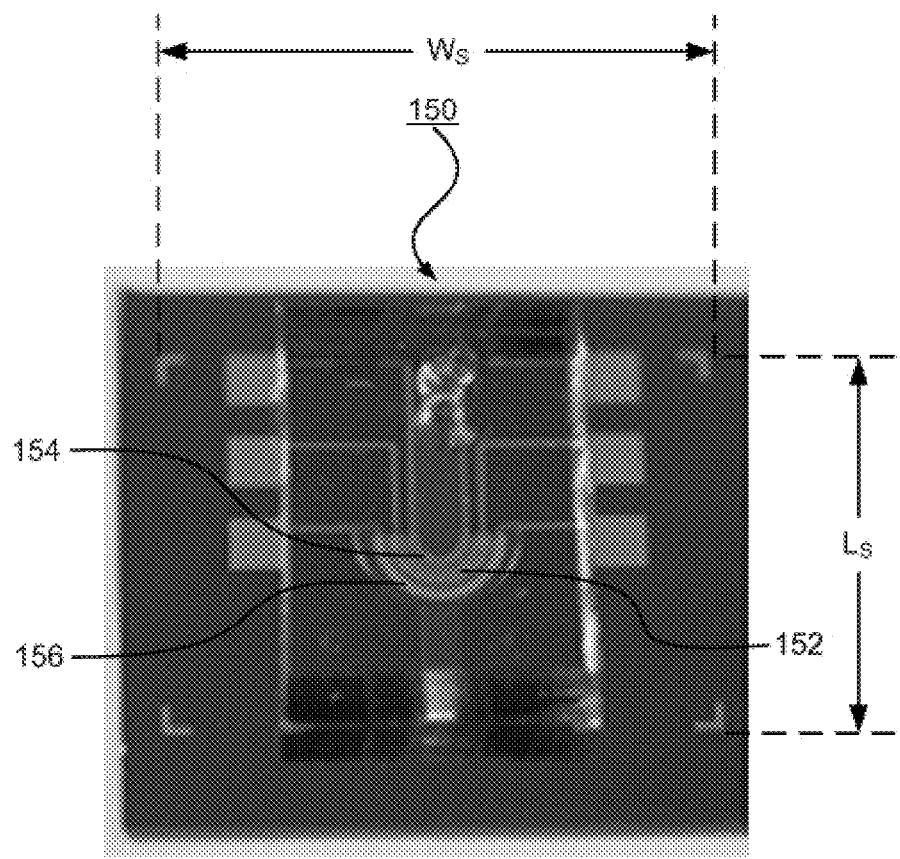
FIGS. 6A through 6C are photographs of a prototype chemical sensor in accordance with yet another embodiment of the present invention.

Referring now to FIG. 6A, an assembled prototype MEMS chemical sensor 150 fabricated under laboratory conditions with microfluidic channel on top of the sensor base is shown. The sensor 150 of the present embodiment has a width Ws of about 16 millimetres (mm) and a length Ls of about 11 mm.

Figure 6B:
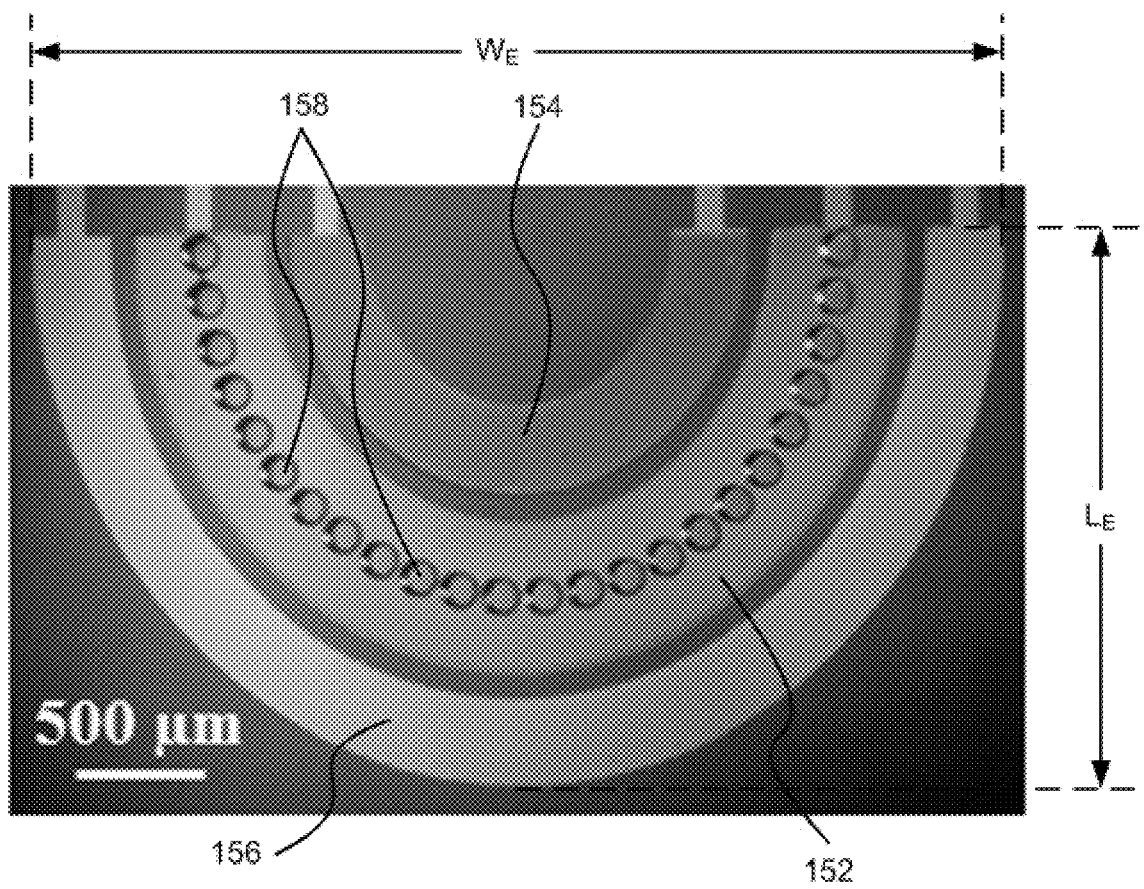

Referring now to FIG. 6B, a semi-circular three-electrode configuration of the prototype chemical sensor 150 captured under an optical microscope is shown. More particularly, a working electrode 152, a reference electrode 154 and a counter electrode 156 of the prototype chemical sensor 150 are shown in FIG. 6B. As can be seen from FIG. 6B, the prototype 150 includes one (1) row of a micropillar working electrode array 158. In the embodiment shown, a separation between the working electrode 152 and the reference electrode 154 is about 0.1 mm and a separation between the working electrode 152 and the counter electrode 156 is about 0.1 mm. In the present embodiment, the three-electrode configuration has a width WE of about 3.8 mm and a length LE of about 1.9 mm.

Figure 6C:
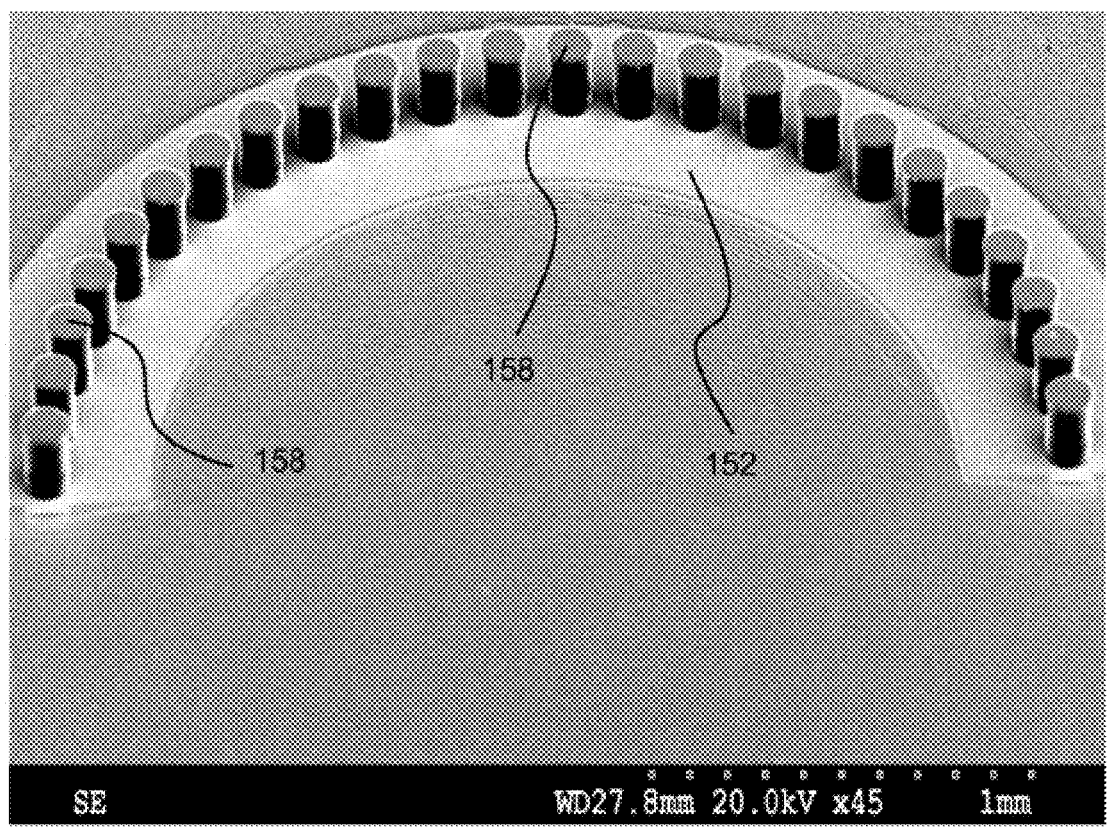

Referring now to FIG. 6C, a scanning electron microscopy (SEM) image of the micropillar working electrode array 158 is shown. As can be seen from FIG. 6C, the micropillar working electrode array 158 of the prototype chemical sensor 150 consists of twenty-four (24) micropillars, each having a diameter of about 100 μm and a height of about 120 μm.

Referring again to FIG. 6A, the prototype chemical sensor 150 was initially characterized with a high-precision probe station to inspect the electrical connections. The probe station consists of two movable probes with tiny metal tips that can be finely controlled in three different directions with the help of a high-resolution optical microscope. The other ends of the two movable probes are connected to a digital multimeter. The electrical connections between two contact pads of each base miniaturized electrode and a respective one of each micropillar electrode were carefully checked to ensure that all the micropillar electrodes are electrically connected to the base working electrode and all the resistance values are consistent.

Figure 7A:
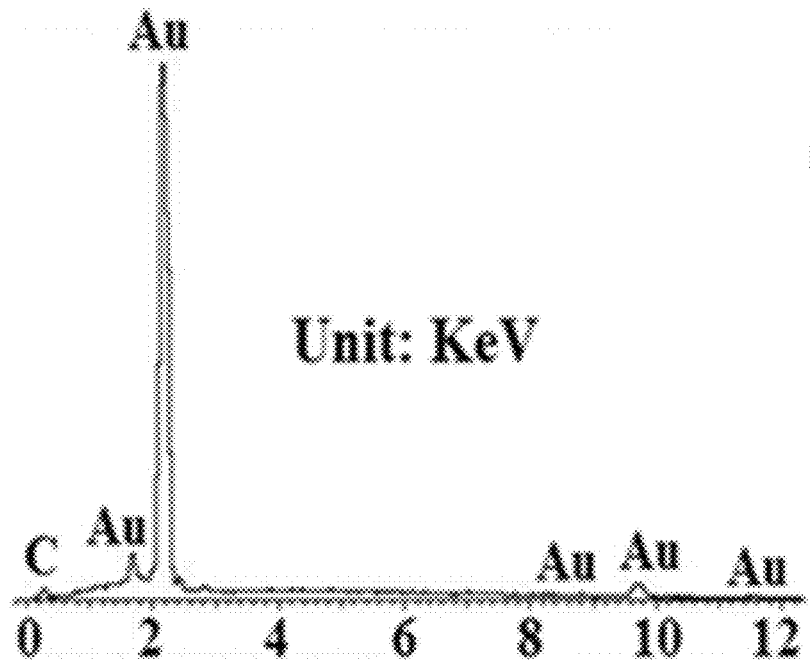
FIGS. 7A and 7B are energy dispersive spectroscopy (EDS) spectrums showing the elemental composition of a top wall and a side wall of a micropillar working electrode of the prototype chemical sensor.
Figure 7B:
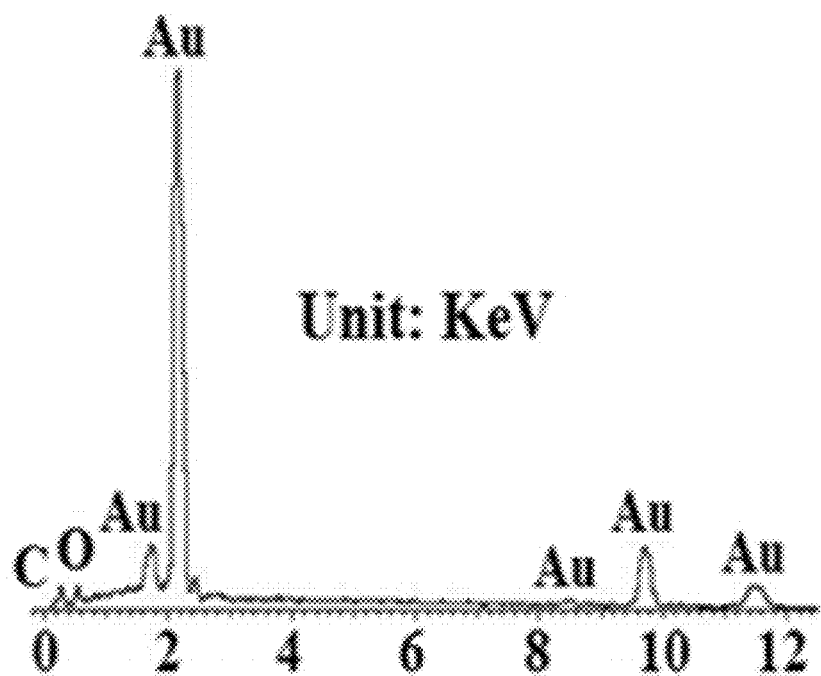

Referring now to FIGS. 7A and 7B, to confirm the coating of the gold layer on the micropillar electrodes, energy dispersive spectroscopy (EDS) analysis was performed to investigate the elemental composition of both the top and side walls of the individual micropillars. EDS spectrum analysis is based on a fundamental principle that when a sample surface is shone on by a beam of high-energy charged particles (e.g. electrons or protons), each element will emit a unique set of X-rays that is highly dependent on the atomic structure of that element. As shown in FIGS. 7A and 7B, the EDS spectrums of the top wall and the side wall, respectively, of one (1) micropillar electrode of the micropillar working electrode array 158 reveal a clear trace of gold element detected, suggesting that a gold thin film was coated on the micropillar electrode. This result confirms the successful fabrication of a three-dimensional micropillar working electrode array by means of MEMS technology. In FIGS. 7A and 7B, the unit KeV represents kiloelectron volt.

The prototype chemical sensor 150 was also electrochemically characterized by comparing the performance of the prototype chemical sensor 150 to commercially available electrodes. The prototype chemical sensor 150 was packaged by using conductive epoxy to connect wires to the contact pads of the three different electrodes. Thereafter, non-conductive epoxy was used to cover the entire prototype chemical sensor 150, leaving only the three electrodes exposed. The packaged prototype chemical sensor 150, a commercially available silver/silver chloride (Ag/AgCl, 3 M NaCl inner electrolyte) reference electrode and a commercially available platinum (Pt) counter electrode were simultaneously immersed into a testing solution. The testing solution was prepared by dissolving a certain amount of potassium ferricyanide ($K_3Fe(CN)_6$) and potassium chloride (KCl) powder into deionized (DI) water to make a final concentration of 2 mM $K_3Fe(CN)_6$ together with 0.2 M KCl. The entire voltammetry cell, which included all three electrodes, was connected to an electrochemical workstation for measurement.

Figure 8A:
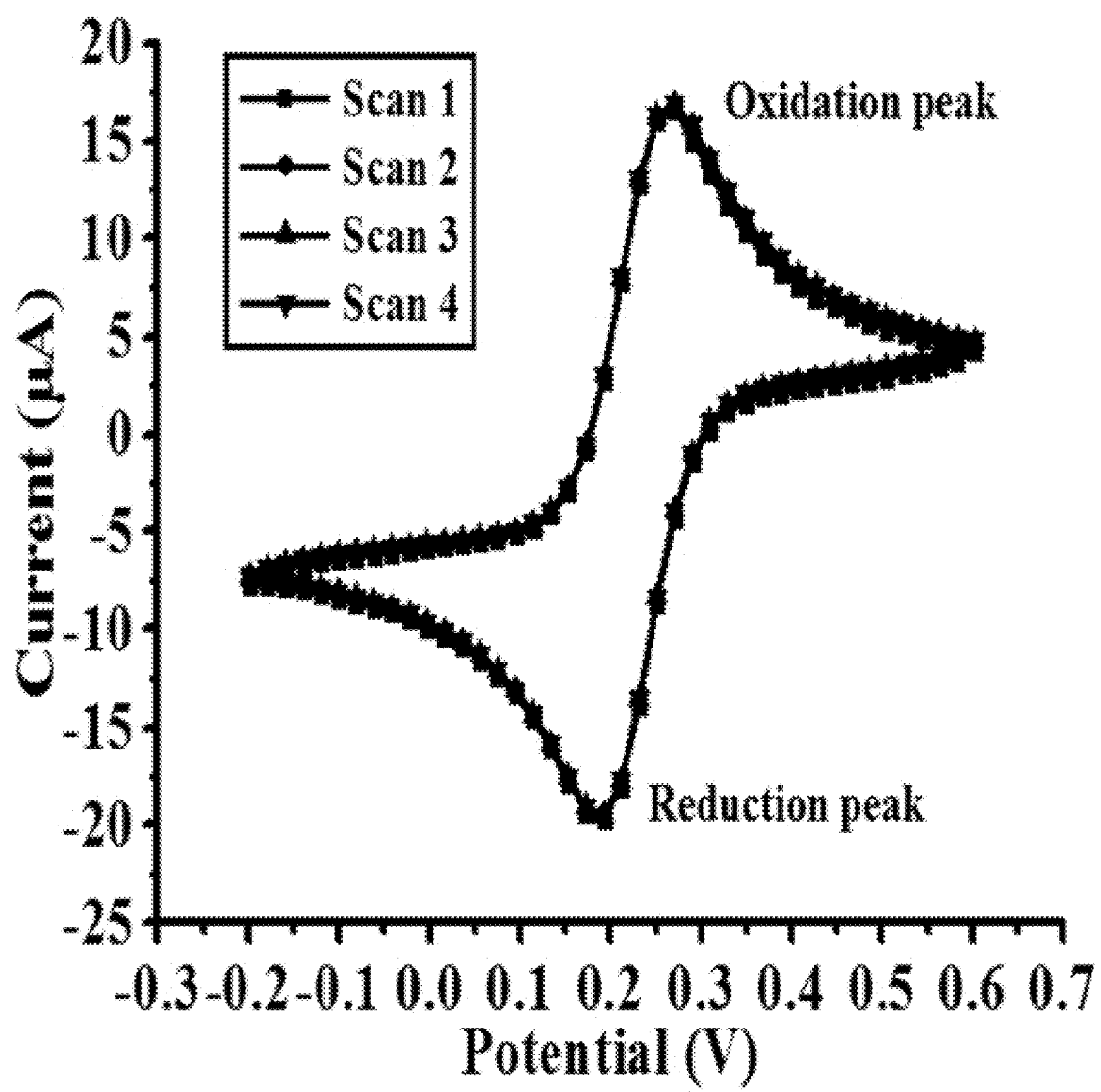
FIGS. 8A through 8C are voltammograms of four repetitive potential scans of cyclic voltammetry on a commercially available Au working electrode, a fabricated Au flat working electrode and a fabricated Au working electrode with micropillar electrode array, respectively, with a commercially available Ag/AgCl reference electrode and a commercially available Pt counter electrode.
Figure 8B:
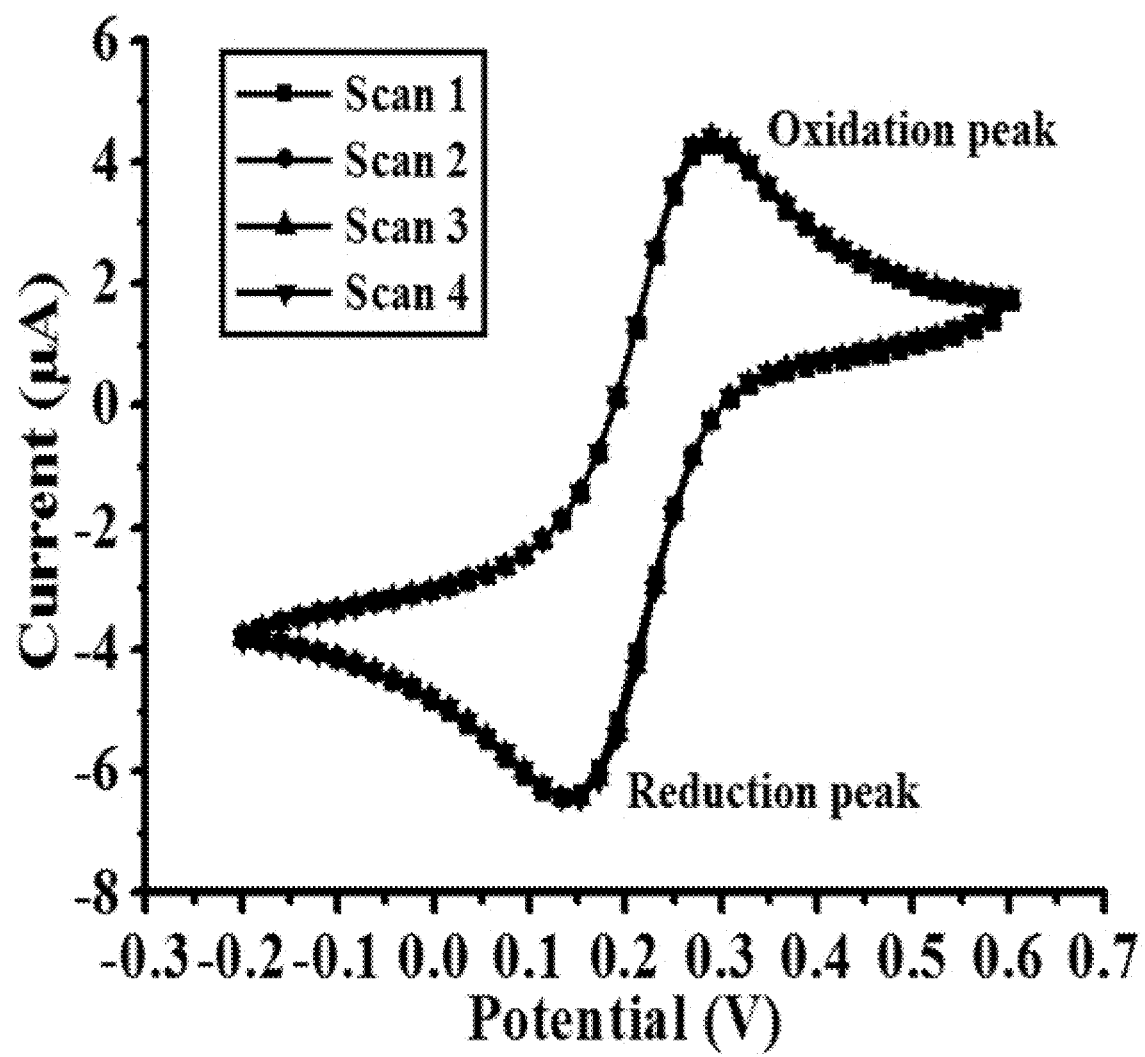
Figure 8C:
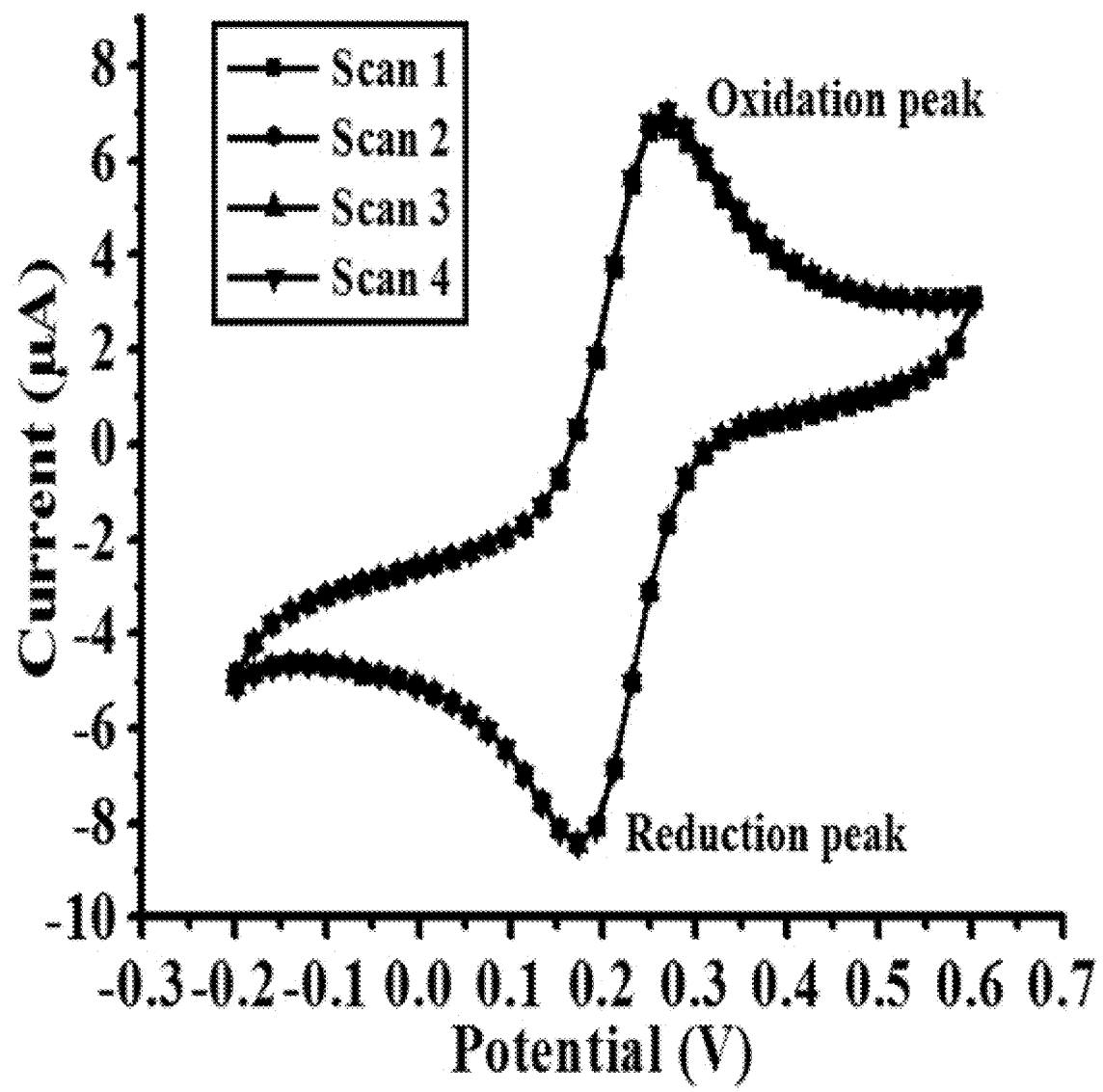

Referring now to FIGS. 8A through 8C, a cyclic voltammetry experiment was firstly performed by continuously scanning a potential forward and backward in a potential range of 0.6 to −0.2 volt (V) (with respect to the commercially available Ag/AgCl reference electrode) at a scan rate of 0.05 volt per second (V/s) on the commercially available Au working electrode, the commercially available Ag/AgCl reference electrode and the commercially available Pt counter electrode. The purpose of conducting such an experiment is to obtain the reference data for comparison when the commercially available Au working electrode is replaced by the fabricated Au working electrode, since commercially available electrode is supposed to have precise dimensions as well as a reliable electrochemical performance. The redox reaction in the testing solution is expressed by equation (1) below:

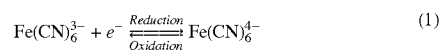

$$Fe(CN)_6^{3-} + e^- \underset{Oxidation}{\overset{Reduction}{\rightleftharpoons}} Fe(CN)_6^{4-} \qquad (1)$$

When the potential is scanned from 0.6 to −0.2 V, ferricyanide ion ($Fe(CN)_6^{3-}$) gains an electron to be reduced into ferrocyanide ion ($Fe(CN)_6^{4-}$), which will generate a reduction peak at a certain potential. The reduction current (with negative sign) decays in an exponential way due to the depletion of $Fe(CN)_6^{3-}$ ion. Similarly, when the potential is scanned from −0.2 to 0.6 V, the previously generated $Fe(CN)_6^{4-}$ ion loses the electron to become $Fe(CN)_6^{3-}$ ion, at which an oxidation peak is produced. The oxidation current also follows an exponential decay analogous to the reduction step.

Voltammograms of four repetitive potential scans of cyclic voltammetry on a commercially available Au working electrode, a commercially available Ag/AgCl reference electrode and a commercially available Pt counter electrode are shown in FIG. 8A. The potentials were measured with respect to the commercially available Ag/AgCl reference electrode. As can be seen from FIG. 8A, during the negative-going scan (from 0.6 to −0.2 V), $Fe(CN)_6^{3-}$ ion was reduced to $Fe(CN)_6^{4-}$ ion, producing a reduction peak near 0.19 V. During the positive-going scan (from −0.2 to 0.6 V), reaction in the vicinity of working electrode surface was reversed to generate an oxidation peak near 0.27 V. Both reduction current and oxidation current showed a similar trend of exponentially decreasing over time. The two undistorted peaks distinctly show evidence of a well-defined redox reaction happening in the testing solution.

Immediately after, voltammograms of four repetitive potential scans were recorded in the same solution by replacing the commercially available Au working electrode with a fabricated Au flat working electrode and the fabricated Au working electrode with micropillar electrode array. By doing so, the feasibility of MEMS-based electrodes for electrochemical application can be verified. Voltammograms of four repetitive scans of cyclic voltammetry on the fabricated Au flat working electrode and the fabricated Au working electrode with micropillar electrode array, together with commercial Ag/AgCl reference electrode and commercial Pt counter electrode, are shown in FIGS. 8B and 8C, respectively. The potentials were measured with respect to the commercially available Ag/AgCl reference electrode. As shown in FIGS. 8B and 8C, both the reduction peak and the oxidation peak of the MEMS chemical sensor without and with the micropillar electrode array are clearly observed in all the potential scans. In addition, repeatability of the MEMS-based chemical sensor is quite favorable in light of the fact that only a tiny amount of inequality in the peak currents was detected among the four scans for both types of the MEMS chemical sensor.

Since cyclic voltammetry was performed in an unstirred testing solution, hydrodynamic convection effect had no effect on the transport of electroactive materials to the working electrode surface. Besides, migration effect, that is the movement of charged particles along an electrical field, also did not contribute to the mass transport given that the concentration of the supporting electrolyte (in this case, 0.2 M KCl) was much higher than the one of electroactive materials (in this case, 0.002 M $K_3Fe(CN)_6$). Therefore, the electroactive species dissolved in the solution were transported to the electrode-solution interface only by diffusion effect. Diffusion is a kind of spontaneous movement under the influence of a concentration gradient. The motivation behind diffusion is related to the second law of thermodynamics, which is to maximize the entropy of the whole system to achieve a homogenous state in the end. Under such conditions, the current response of the cyclic voltammetric experiment is directly correlated with the concentration gradient near the working electrode surface. The peak current is derived from the Randles-Sevcik equation (2) shown below:

$$i_p = 0.4463 \frac{n^{3/2} F^{3/2}}{R^{1/2} T^{1/2}} D^{1/2} v^{1/2} A C \quad (2)$$

where $i_p$ represents peak current (A), n represents the number of electrons transferred in the redox reaction, F represents Faraday's constant (C/mol), R represents gas constant (V·C/mol·K), represents temperature (K), D represents diffusion coefficient ($cm^2/s$), v represents scan rate (V/s), A represents electrode area ($cm^2$), and C represents bulk concentration ($mol/cm^3$).

Figure 9A:
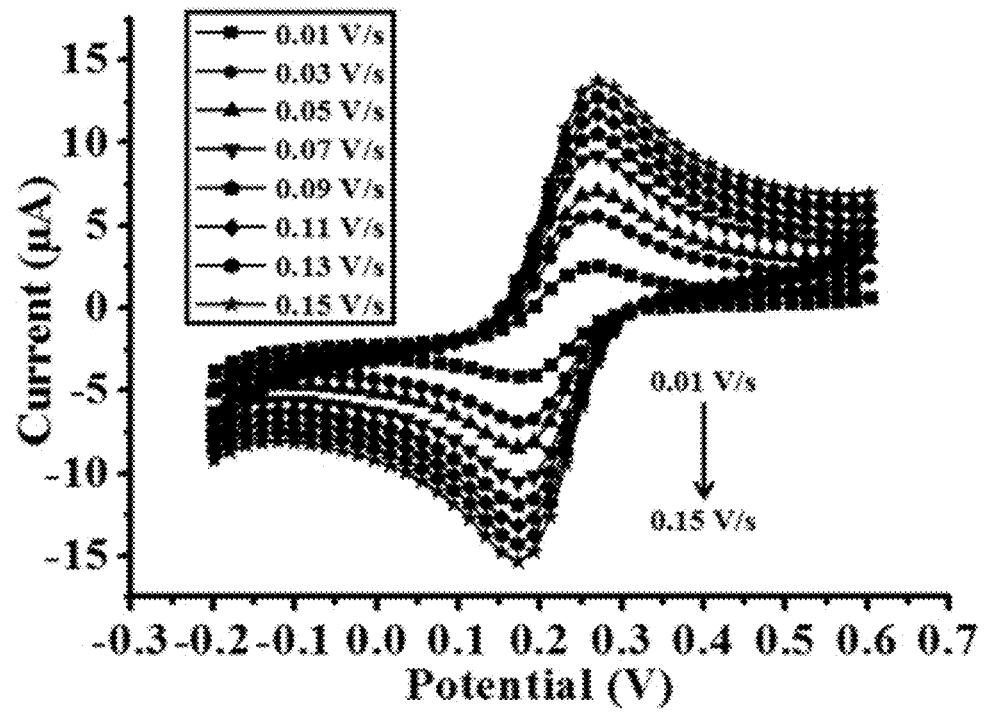
FIG. 9A shows cyclic voltammograms obtained under different scan rates.
Figure 9B:
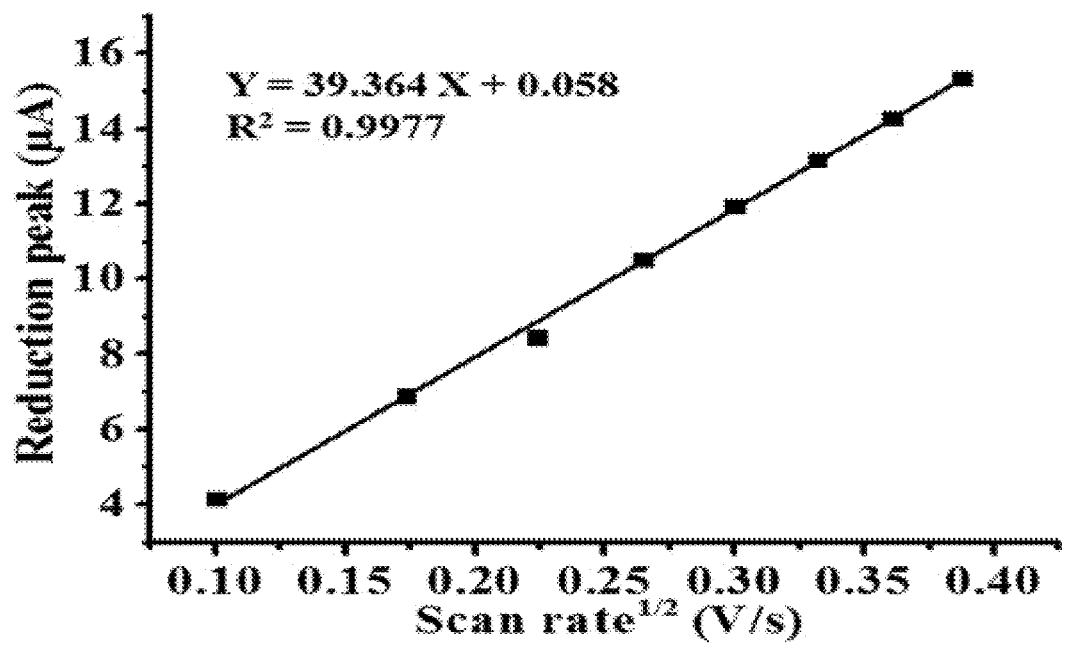
FIG. 9B shows a fitting curve of the magnitude of the reduction peak with respect to the square root of the scan rate.

Equation (2) suggests that the magnitude of peak current should be linearly propositional to the square root of the scan rate if other parameters remain unchanged. For the MEMS chemical sensor with the micropillar electrode array, a series of cyclic voltammetric experiments were further performed by only varying the scan rate of the experimental condition. FIG. 9A shows eight cyclic voltammograms where the scan rate was increased from 0.01 to 0.15 V/s at intervals of 0.02 V/s. Despite the change of scan rate, the reduction peak as well as the oxidation peak is easily identifiable with only a tiny shift in peak potential. FIG. 9B shows the relationship between the magnitude of the reduction peak and the square root of the scan rate. The fitting curve shows good linear correlation ($R^2=0.9977$), which is in agreement with the Randles-Sevcik equation. These results demonstrate that the fabricated MEMS chemical sensor with micropillar working electrode array is capable of accurately tracking the redox reactions that happen in the solution.

In order to investigate the performance of the prototype sensor for heavy metal detection, a square wave anodic stripping voltammetry (SWASV) experiment was performed to quantify the analytical response of the sensor to different heavy metal ions. All the chemicals used during the experiment were of analytical grade. DI water collected from a Milli-Q system was used for preparation of all the solutions. Heavy metal solutions with different concentrations were prepared from stock solution (1000 mg/L, atomic absorption standard solution). Acetate buffer of 0.1 M (pH 4.6) was used as the supporting electrolyte. All SWASV experiments were carried out in a similar sequence. Initially, a certain deposition potential was applied to the micropillar working electrode array for a period of time (deposition time). At the end of the quiescent period, a voltammogram was recorded in a certain potential window under the square wave voltammetry mode with optimal frequency, amplitude and step potential. Before the next measurement, a conditioning potential was applied for a certain period of time (conditioning time) to remove any residual metal left on the electrode surface.

Figure 10A:
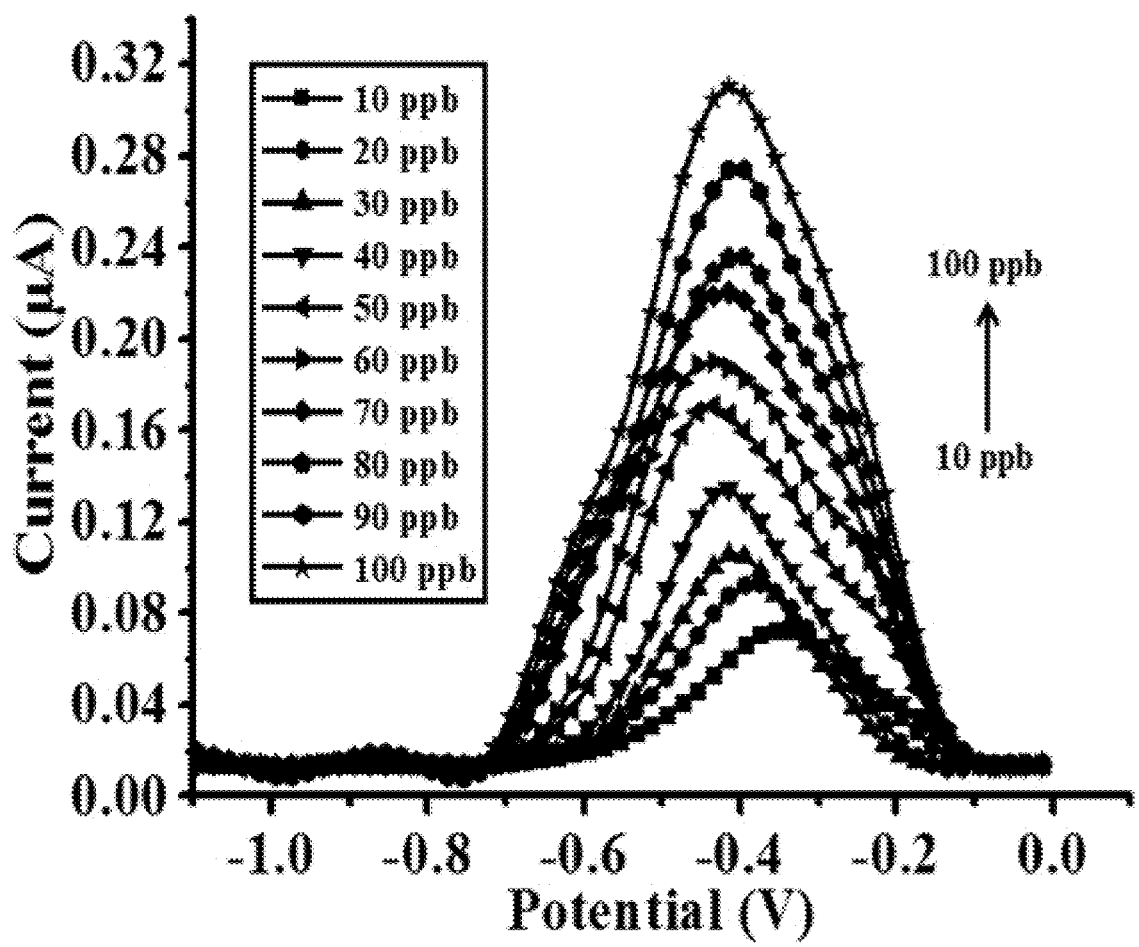
FIGS. 10A and 10B show SWASV voltammograms obtained from a prototype sensor without microfluidic channel and a corresponding calibration curve of stripping peak currents with respect to different lead concentrations.
Figure 10B:
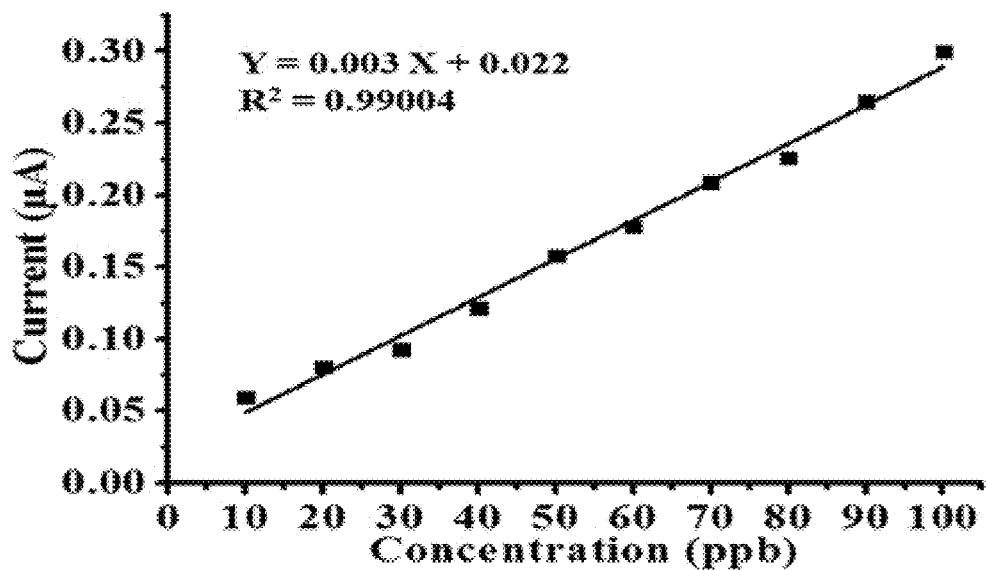

A first investigation was performed to check the analytical performance of the prototype sensor for lead detection without using a microfluidic channel. SWASV experiments were performed in an unstirred condition with a deposition potential of −1.2 V, a deposition time of 300 seconds (s), a quiescent time of 10 s, a frequency of 50 hertz (Hz), an amplitude of 50 millivolt (mV), a step potential of 5 mV, a conditioning potential of 0.3 V and a conditioning time of 600 s. As shown in FIG. 10A, a series of voltammograms are displayed with increased lead concentrations from 10 to 100 ppb (1 ppb=1 μg/L). The lead stripping peaks are legibly located around −0.4 V with respect to the potential of the fabricated on-chip Ag/AgCl reference electrode. The corresponding calibration curve of the peak current with respect to different lead concentrations shown in FIG. 10B exhibits good linearity ($R^2=0.99004$). Analytical sensitivity of 3 nA/ppb and limit of detection (LOD) of 0.8 ppb were obtained.

Figure 11A:
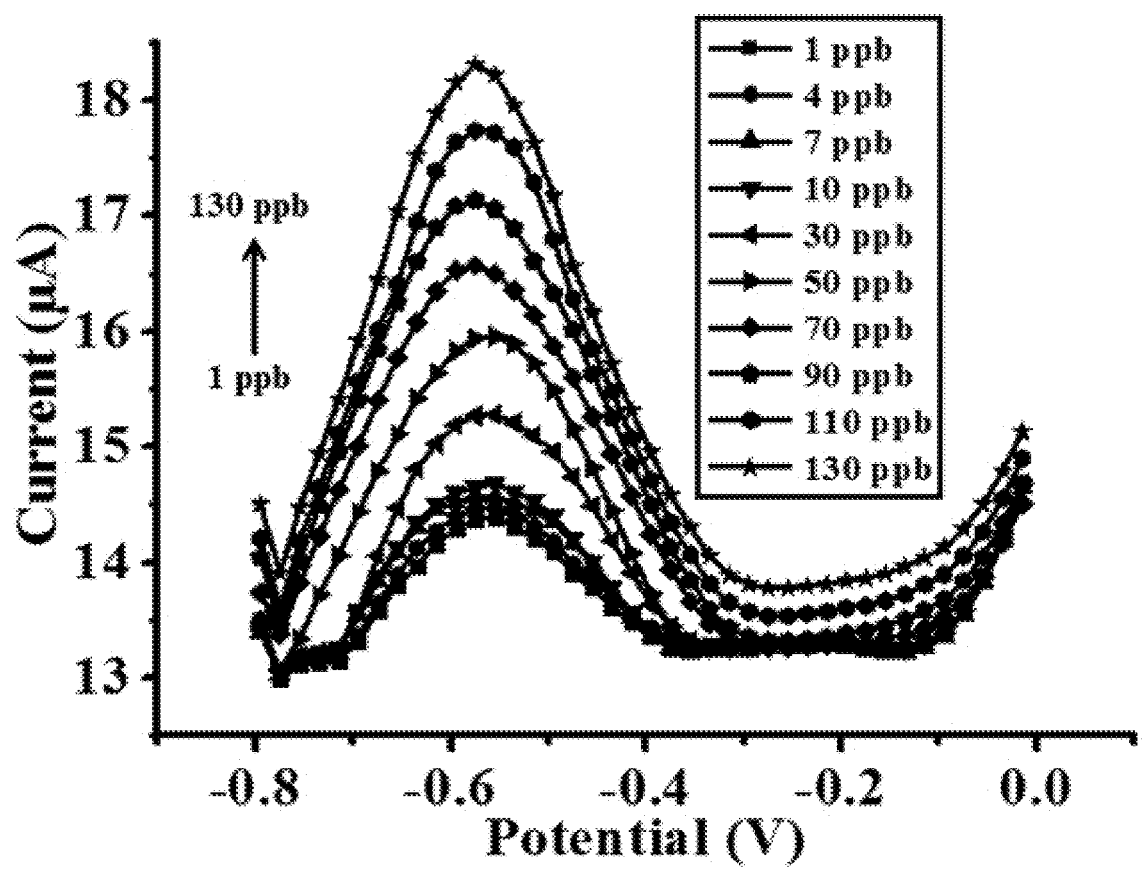
FIGS. 11A and 11B show SWASV voltammograms obtained from a prototype sensor with microfluidic channel and a corresponding calibration curve of stripping peak currents with respect to different lead concentrations.
Figure 11B:
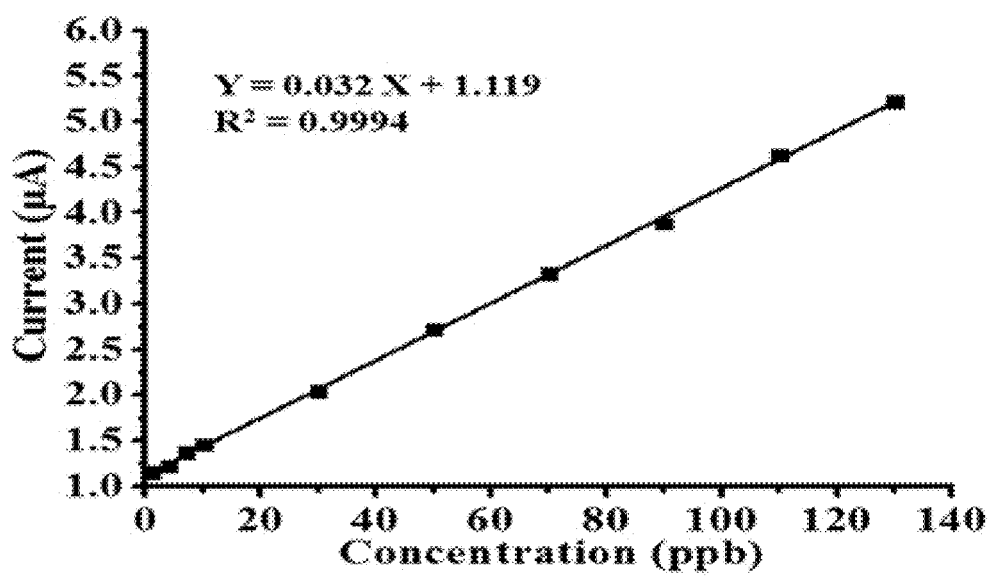

The second investigation was performed to examine the analytical performance of the prototype sensor for lead detection when microfluidic channel was present. Deposition of the SWASV experiments was conducted by accurately dispensing lead and bismuth solution into the microfluidic channel under a selected flow rate. After optimization, measurement parameters were determined as a deposition potential of −0.8 V, a deposition time of 30 s, a quiescent time of 5 s, a frequency of 50 Hz, an amplitude of 50 mV, a step potential of 5 mV, a conditioning potential of 0 V and a conditioning time of 120 s. FIG. 11A shows the voltammograms recorded by elevating the lead concentration from 1 to 130 ppb. Well-defined stripping peaks are observed near −0.55 V with respect to the fabricated on-chip Ag/AgCl reference electrode. The potential shift is probably due to the presence of bismuth ions during deposition as well as the change in thickness of the reference electrode during fabrication. FIG. 11B shows an excellent linear relationship ($R^2=0.9994$) between the stripping peak currents and the lead concentrations. High analytical sensitivity of 32 nA/ppb and a gratifying LOD of 0.2 ppb were achieved. In comparison to the previous investigation, analytical performance of the sensor presented significant enhancement in terms of a shorter deposition time, a higher sensitivity and a higher LOD. The reason may be that in the previous investigation, the measurement was carried out in an unstirred condition, in which only diffusion effect contributed to the mass transport of lead metal ions to the working electrode surface. However, the current investigation was performed with the testing solution being continuously dispensed into the microfluidic channel, where convection effect—more vigorous than the diffusion effect, played a prominent role in the mass transport of lead ions.

Figure 12A:
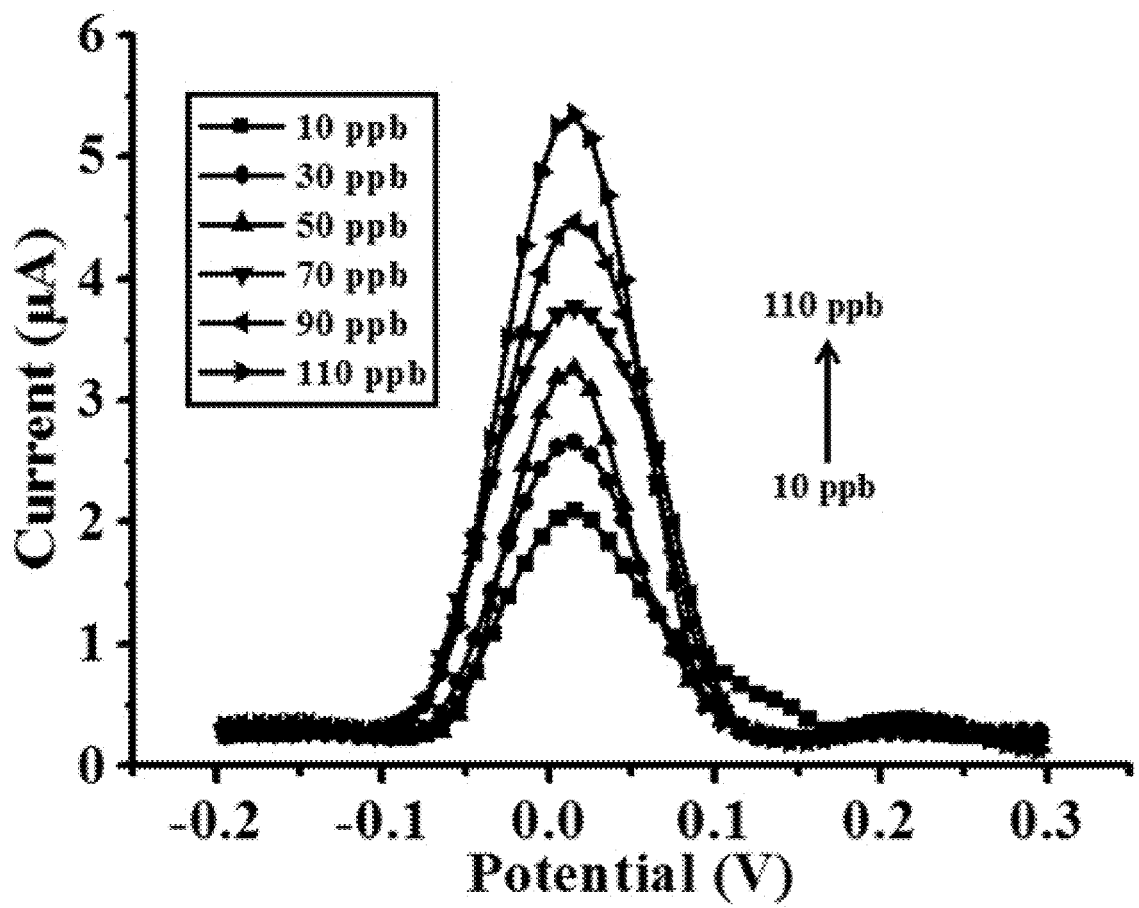
FIGS. 12A and 12B show SWASV voltammograms obtained from a prototype sensor with microfluidic channel and a corresponding calibration curve of stripping peak currents with respect to different copper concentrations.
Figure 12B:
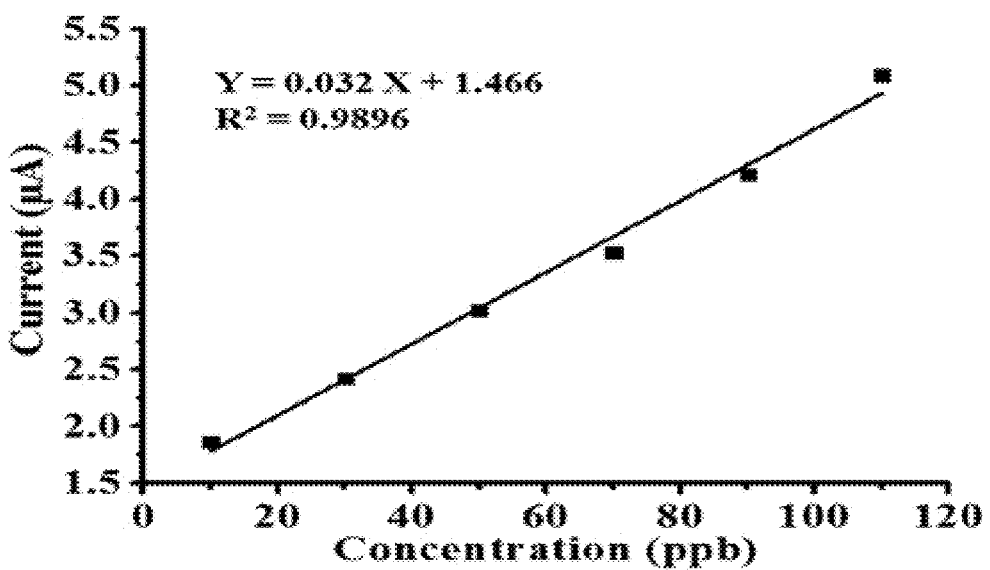

A third investigation was performed to explore the possibility of the prototype sensor for copper detection. Since different heavy metal ions have different stripping potential windows, the measurement parameters had to be re-evaluated to find the optimal values. After optimization, the selected parameters were a deposition potential of −0.3 V, a deposition time of 40 s, a quiescent time of 5 s, a frequency of 20 Hz, an amplitude of 45 mV, a step potential of 5 mV, a conditioning potential of 0.02 V and a conditioning time of 180 s. A series of SWASV voltammograms shown in FIG. 12A were recorded when the copper concentration was increased from 10 to 110 ppb. Undistorted stripping peaks were located near 0.2 V with respect to the fabricated on-chip Ag/AgCl reference electrode. FIG. 12B shows the calibration curve, with good linearity ($R^2$=0.9896), of the peak currents versus the different copper concentrations. An analytical sensitivity of 32 nA/ppb and a favorable LOD of 0.4 ppb were obtained.

Table 1 below summarizes the analytical performance of the prototype sensor for lead and copper detection. The experimental results demonstrate the capability of the MEMS chemical sensor for on-site/in-situ heavy metal detection.

TABLE 1

| Detection Target | Usage of Microfluidic Channel | Deposition Time (s) | Analytical Sensitivity (nA/ppb) | Limit of Detection (ppb) |
| --- | --- | --- | --- | --- |
| Lead | No | 300 | 3 | 0.8 |
| Lead | Yes | 30 | 32 | 0.2 |
| Copper | Yes | 40 | 32 | 0.4 |

As is evident from the foregoing discussion, the present invention provides a miniaturized, sensitive and disposable chemical sensor for on-site/in-situ heavy metal detection. Advantageously, fabrication of the chemical sensor of the present invention can be fully achieved by using standardized MEMS techniques like thin-film deposition, photolithographic patterning, wet etching or dry etching etc. Miniaturization of the chemical sensor of the present invention in the range of several micrometers to a few centimeters offers a number of operational benefits such as higher resonance frequency, higher sensitivity, better linearity and a wider dynamic range. In general, measuring accuracy of macro-sized instruments generate substantial drift when subjected to external disturbances, e.g. changes in the ambient condition, increased noise levels and abrupt vibrations and so on, whereas these unexpected perturbations have less impact on the signal obtained with MEMS systems. Moreover, seamless combination of micromechanical parts with electronic circuitry at a single wafer level produces an integrated MEMS product with fast computing and processing capabilities. In addition, the fine three-dimensional features may be precisely controlled and manufactured in a repeatable way with MEMS fabrication techniques. The involvement of MEMS fabrication also brings about a number of other advantages such as a low manufacturing cost of each individual device due to the simplicity of MEMS batch fabrication, light weight and compact structures due to MEMS miniaturization.

Further advantageously, by providing a plurality of protrusions extending into a fluid flow path in the reaction chamber beyond a boundary layer of the fluid flow path, the problem of low capture efficiency of heavy metal ions absorbed by a sensing electrode in conventional chemical sensors is addressed. This is because moving flow always generates a relatively thick boundary layer at both top and bottom surfaces of a microfluidic channel. If a working electrode is submerged in the boundary layer, just like in the case of a planar electrode, the majority of the charged ions will simply be washed away with the moving flow, resulting in a mass of sample solution being wasted. On the contrary, the standing columnar electrodes extend the sensing area outside the boundary layer, exposing the electrode surface directly to movable ions in such a way that the fraction of metal ions captured by the working electrode is significantly increased. As such, the total volume of testing sample that is required for evaluating pollution levels of heavy metals with the chemical sensor of the present invention can be minimized and the sensitivity along with the limit of detection of the chemical sensor can be magnified if a limited quantity of sample solution is being tested.

The chemical sensor of the present invention may be used to routinely monitor heavy metal pollution levels of surface water sources before transporting to a water treatment plant. With large-scale distribution of cost-effective, reliable and sensitive MEMS chemical sensors, it may be possible to continuously provide real-time information. This would lower water treatment expenditure since pollution of source water can be quickly identified before the heavy metal contamination spreads and cleaning up less-contaminated source water is much more easy, efficient and economical compared to dealing with heavily polluted water. Additionally, labor-intensive and time-consuming water sample collection may be done away with, improving the efficiency of data acquisition and transmission.

Currently, the quality of portable water after distribution to consumers at home, work or any other public place cannot be guaranteed because physical, chemical and biological purifications are only conducted at a treatment plant. Accordingly, the chemical sensor of the present invention may also be used to help end-users obtain information on the quality of piped water.

While preferred embodiments of the invention have been illustrated and described, it will be clear that the invention is not limited to the described embodiments only. Numerous modifications, changes, variations, substitutions and equivalents will be apparent to those skilled in the art without departing from the scope of the invention as described in the claims.

Further, unless the context clearly requires otherwise, throughout the description and the claims, the words "comprise", "comprising" and the like are to be construed in an inclusive as opposed to an exclusive or exhaustive sense; that is to say, in the sense of "including, but not limited to".

The invention claimed is:

1. A chemical sensor, comprising:
an inlet;
a chamber in fluid communication with the inlet;
an outlet in fluid communication with the chamber;
a working electrode provided in the chamber, wherein the working electrode comprises a plurality of protrusions extending into a fluid flow path in the chamber beyond a boundary layer of the fluid flow path;
a reference electrode;
a counter electrode;
a plurality of contact pads electrically connected to respective ones of the working electrode, the reference electrode and the counter electrode;
a first microfluidic channel coupling the inlet to the chamber; and
a plurality of subchannels interfacing the first microfluidic channel and the working electrode,
wherein the protrusions are provided in a parabolic arrangement, and
wherein the plurality of subchannels are configured to guide the fluid flow path towards the plurality of protrusions.

2. The chemical sensor of claim 1, wherein the protrusions are arranged in an array.

3. The chemical sensor of claim 1, wherein each of the protrusions comprises a column of micro dimensions.

4. The chemical sensor of claim 3, wherein each column has a height of between about 10 microns (µm) and about 1000 µm.

5. The chemical sensor of claim 1, further comprising a first portion and a second portion, wherein the inlet and the outlet are provided in the first portion, wherein the working electrode, the reference electrode and the counter electrode are provided in the second portion, and wherein the chamber is defined between the first portion and the second portion.

6. The chemical sensor of claim 1, further comprising a second microfluidic channel coupling the chamber to the outlet.

7. The chemical sensor of claim 1, further comprising a substrate, wherein the reference electrode and the counter electrode are provided on the substrate.

8. The chemical sensor of claim 7, wherein the working electrode is provided on the substrate and comprises an electrically conductive layer, a plurality of microcolumns provided on the electrically conductive layer and an electrically conductive material deposited on the microcolumns.

9. The chemical sensor of claim 7, wherein the working electrode is provided in the substrate.

10. The chemical sensor of claim 1, wherein a surface area of the counter electrode is at least 1.5 times a surface area of the reference electrode.

11. The chemical sensor of claim 1, wherein a surface of the protrusions is modified by at least one of a plurality of metallic nanoparticles, a two-dimensional material and a plurality of deoxyribonucleic acid/ribonucleic acid (DNA/RNA) molecules.

* * * * *